US008455631B2

(12) United States Patent
Ward

(10) Patent No.: US 8,455,631 B2
(45) Date of Patent: *Jun. 4, 2013

(54) *TRICHODERMA* PROMOTER

(75) Inventor: Michael Ward, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/217,499

(22) Filed: Aug. 25, 2011

(65) Prior Publication Data

US 2011/0312031 A1    Dec. 22, 2011

Related U.S. Application Data

(62) Division of application No. 12/193,614, filed on Aug. 18, 2008, now Pat. No. 8,044,192.

(60) Provisional application No. 60/971,807, filed on Sep. 12, 2007.

(51) Int. Cl.
*C07H 21/04* (2006.01)
*C12N 1/15* (2006.01)

(52) U.S. Cl.
USPC ..................................... 536/24.1; 435/254.11

(58) Field of Classification Search
None
See application file for complete search history.

(56) References Cited

U.S. PATENT DOCUMENTS

| | | | |
|---|---|---|---|
| 5,364,770 | A | 11/1994 | Berka et al. |
| 5,989,870 | A | 11/1999 | Nakari et al. |
| 6,001,595 | A | 12/1999 | Ilmén et al. |
| 6,022,725 | A | 2/2000 | Fowler et al. |
| 6,103,490 | A | 8/2000 | Berka et al. |
| 6,268,328 | B1 | 7/2001 | Mitchinson et al. |
| 6,509,171 | B1 | 1/2003 | Berka et al. |
| 6,562,612 | B2 | 5/2003 | Jones et al. |
| 6,590,078 | B2 | 7/2003 | Ward et al. |

FOREIGN PATENT DOCUMENTS

| | | |
|---|---|---|
| EP | 0 215 594 A2 | 3/1987 |
| EP | 0 244 234 A2 | 11/1987 |
| EP | 0 351 029 A1 | 1/1990 |
| WO | WO 96/00787 A1 | 1/1996 |
| WO | WO 01/51643 A1 | 7/2001 |
| WO | WO 03/089621 A2 | 10/2003 |
| WO | WO 2005/001036 A2 | 1/2005 |
| WO | WO 2006/060062 A2 | 6/2006 |
| WO | WO 2008/076322 A2 | 6/2008 |

OTHER PUBLICATIONS

U.S. Appl. No. 10/992,187, filed Sep. 22, 2005, Baldwin et al.
U.S. Appl. No. 11/255,794, filed Feb. 23, 2006, Stafford et al.
U.S. Appl. No. 11/108,088, filed Feb. 23, 2006, Davidson et al.
U.S. Appl. No. 60/984,430, filed Nov. 1, 2007, Bao et al.
*Altschul, S.F. et al. "Basic local alignment search tool." *J. Mol. Biol* 215(3): 403-410, 1990.

*Bagdasarian, M.M. et al. "Activity of the hybrid trp-lac (tac) promoter of *Escherichia coli* in *Pseudomonas putida*. Construction of broad-host-range, controlled-expression vectors." *Gene* 26(2-3): 273-282, Dec. 1983.
*Berka, R.M. et al. "*Aspergillus niger* var. *awamori* as a host for the expression of heterologous genes." in *Applications of Enzyme Biotechnology*, edited by J.W. Kelly et al., pp. 273-292. New York: Plenum Press, 1991.
*Berka, R.M. et al. "Molecular cloning and deletion of the gene encoding aspergillopepsin A from *Aspergillus awamori*." *Gene* 86(2): 153-162, Feb. 14, 1990.
*Bower, B. et al. "Hyperexpression and glycosylation of *Trichoderma reesei* EG III." In *Carbohydrases from Trichoderma reesei and other micro-organisms*, edited by M. Claeyssens et al., pp. 327-334. Cambridge, England: Royal Society of Chemistry, 1998.
*Campbell, E.I. et al. "Improved transformation efficiency of *Aspergillus niger* using the homologous niaD gene for nitrate reductase." *Current Genetics* 16(1): 53-56, Jul. 1, 1989.
*Cao, Q.N. et al. "Penicillopepsin-JT2, a recombinant enzyme from *Penicillium janthinellum* and the contribution of a hydrogen bond in subsite S3 to k(cat)." *Protein Sci* 9(5): 991-1001, May 1, 2000.
*Chambergo F.S. et al. "Elucidation of the metabolic fate of glucose in the filamentous fungus *Trichoderma reesei* using expressed sequence tag (EST) analysis and cDNA microarrays" *Journal of Biological Chemistry*, 227(16):13983-13988, Apr. 19, 2002.
*Database EMBL [Online], Nov. 1, 2003 "tric083xm17.b11T. reesei mycelialculture, version Oct. 6, 2003 *Hypocrea jecorina* cDNA clone tric083xm17, mRNA sequence." retreived from EBI accession No. EMBL: CF885793.
*Database Geneseq [Online], Mar. 13, 2001 "*Trichoderma reesei* est seq ID No. 7499", retrieved from EBI accession No. GSN: AAF14976.
*Database JGI T. Reesei v1.0 [Online], Joint Genome Institute; version 1.5.4 Jun. 1, 2007, "*T.reesei* v.1.0" XP002506721 retrieved from http://genome.JGI-psf.org/CGI-bin/dispgenemodel?db=trire1 &tid=43977 accession No. protein ID: 43977 Database accession No. estExt_fgenesh1-pg.C_30027.
*Deuschle, U. et al. "Promoters of *Escherichia coli*: a hierarchy of in vivo strength indicates alternate structures." *The Embo Journal* 5(11): 2987-2994, Nov. 1986.
*Diener S.E. et al. "Characterization of the protein proessing and secretion pathways in a comprehensive set of expressed sequence tags from *Trichoderma reesei*" *Fems Microbiology Letters*, 230(2): 275-282, Jan. 30, 2004.
*Foreman, P.K. et al. "Transcriptional Regulation of Biomass-degrading Enzymes in the Filamentous Fungus *Trichoderma reesei*." *J. Biol. Chem.* 278(34): 31988-31997, Aug. 22, 2003.
*Harkki, A. et al. "Genetic engineering of *Trichoderma* to produce strains with novel cellulase profiles." *Enzyme Microb. Technol* 13(3): 227-33, Mar. 1991.
*Harkki, A. et al. "A Novel Fungal Expression System: Secretion of Active Calf Chymosin from the Filamentous Fungus *Trichoderma reesei*." *Bio/Technology* 7(6): 596-603, Jun. 1989.

(Continued)

*Primary Examiner* — Michele K Joike
(74) *Attorney, Agent, or Firm* — Danisco US Inc.

(57) ABSTRACT

A promoter for use in producing proteins in filamentous fungal host cells is provided. In one embodiment, the promoter comprises SEQ ID NO:1, or a variant or a truncated form thereof that has promoter activity in a host cell. Also provided are recombinant nucleic acids, vectors containing the promoter and host cells containing a recombinant nucleic acid or vector. Methods of producing a protein using the host cells are also provided.

20 Claims, 5 Drawing Sheets

OTHER PUBLICATIONS

*Hopwood, D.A. et al. "Regulation of gene expression in antibiotic-producing *Streptomyces*." In *Regulation of gene expression—25 years on*, edited by I.R. Booth et al., pp. 251-276. Cambridge, England: Cambridge UP, 1986.

*Ilmén, M. et al. "Regulation of cellulase gene expression in the filamentous fungus *Trichoderma reesei*." *Applied and Environmental Microbiology* 63(4): 1298-306, Apr. 1997.

*Innis, M. A. et al. "Expression, Glycosylation, and Secretion of an *Aspergillus* glucoamylase by *Saccharomyces cerevisiae*." *Science* 228(4695): 21-26, Apr. 5, 1985.

*Karlin, S. et al. "Applications and statistics for multiple high-scoring segments in molecular sequences." *Proc. Natl. Acad. Sci. USA* 90(12): 5873-7, Jun. 15, 1993.

*Kelly, J.M. et al. "Transformation of *Aspergillus niger* by the amdS gene of *Aspergillus nidulans*." *EMBO J.* 4(2): 475-479, Feb. 1985.

*Keranen, Sirkka et al. "Production of recombinant proteins in the filamentous fungus *Trichoderma reesei*" Current Opinion in Biotechnology, London, GB, 6(5): 534-537 Jan. 1, 1995.

*Labes, G. et al. "Isolation and characterization of a strong promoter element from the *Streptomyces ghanaensis* phage I19 using the gentamicin resistance gene (aacC1) of Tn 1696 as reporter." *Microbiology* (Reading, England) 143(Pt. 5): 1503-12, May 1997.

*Mach, R.L. et al. "Regulation of gene expression in industrial fungi: *Trichoderma*." *Applied microbiology and biotechnology* 60(5): 515-522, Jan. 2003.

*Machida, M. et al. "Genome sequencing and analysis of *Aspergillus oryzae*." *Nature* 438(7071): 1157-61, 2005.

*Nakamura, Y. et al. "Codon usage tabulated from international DNA sequence databases: status for the year 2000." *Nucl. Acids Res.* 28(1): 292, Jan. 1, 2000.

*Needleman, S.B. et al. "A general method applicable to the search for similarities in the amino acid sequence of two proteins." *J. Mol. Biol* 48(3): 443-53, Mar. 1970.

*Nevalainen, K.M.H. et al. "The Molecular Biology of *Trichoderma* and its Application to the Expression of Both Homologous and Heterologous Genes." In *Molecular Industrial Mycology*, edited by S.A. Leong et al., pp. 129-148. New York: Marcel Dekker, 1991.

*Nunberg, J.H. et al. "Molecular cloning and characterization of the glucoamylase gene of *Aspergillus awamori*." *Mol. Cell. Biol.* 4(11): 2306-2315, Nov. 1, 1984.

*Paloheimo, M. et al. "High-Yield Production of a Bacterial Xylanase in the Filamentous Fungus *Trichoderma reesei* Requires a Carrier Polypeptide with an Intact Domain Structure." *Appl. Environ. Microbiol.* 69(12): 7073-7082, Dec. 1, 2003.

*Pearson, W.R. et al. "Improved Tools for Biological Sequence Comparison." *Proc. Natl. Acad. Sci. USA* 85(8): 2444-2448, Apr. 15, 1988.

*Penttilä, M. et al. "A versatile transformation system for the cellulolytic filamentous fungus *Trichoderma reesei*." *Gene* 61(2): 155-64, 1987.

*Pourquié, J. et al. "Scale up of cellulase production and utilization." In *Biochemistry and Genetics of Cellulose Degradation*, edited by J.P. Aubert et al., pp. 71-86. London: Academic Press, 1988.

*Pulido, D. et al. "*Bacillus subtilis* phage φ29 main promoters are efficiently recognized in vivo by the *Streptomyces lividans* RNA polymerase." *Gene* 49(3): 377-382, 1986.

*Punt, P.J. et al. "Transformation of *Aspergillus* based on the hygromycin B resistance marker from *Escherichia coli*." *Gene* 56(1): 117-24, 1987.

*Saarelainen, R. et al. "Expression of Barley Endopeptidase B in *Trichoderma reesei*." *Appl. Environ. Microbiol.* 63(12): 4938-4940, Dec. 1, 1997.

*Schmitt-John, T. et al. "Promoter constructions for efficient secretion expression in *Streptomyces lividans*." *Appl. Microbiol. Biotechnol.* 36(4): 493-498, Jan. 1, 1992.

*Sheir-Neiss, G. et al. "Characterization of the secreted cellulases of *Trichoderma reesei* wild type and mutants during controlled fermentations." *Applied Microbiology and Biotechnology* 20(1): 46-53, Jul. 1, 1984.

*Smith, T.F. et al. "Comparison of biosequences." *Adv. Appl. Math* 2: 482-489, 1981.

*Ward, J.M. et al. "Construction and characterisation of a series of multi-copy promoter-probe plasmid vectors for *Streptomyces* using the aminoglycoside phosphotransferase gene from Tn5 as indicator." *Molecular and General Genetics* 203(3): 468-478, Jun. 1, 1986.

*Yelton, M.M. et al. "Transformation of *Aspergillus nidulans* by using a trpC plasmid." *Proc. Natl. Acad. Sci. U.S.A* 81(5): 1470-4, Mar. 1984.

'Henrique-Silva et al. Two Regulatory Regions Controlling Basal and Cellulose-Induced Expression of the Gene Encoding Cellobiohydrolase I of *Trichoderma* Adjacent to Its TATA box. Biochemical and Biophysical Research Communications vol. 228, Issue 2, Nov. 12, 1996, pp. 229-237.

SEQ ID NO:1

```
tggcaagtatctgctggaaaaggcccgcgtggccgattactatgtcgacccgtccatcccccattgcaatgtcgaggcggacaagctgtggga
gctgagtgtcaaggcagttgactgttgactgtaggaatgacctgtcaggagacgacggaaattacaagatgatcttgatgtcgaagatggaaattattgcagtgag
atgtgaacaagactaggtatacttagcaaaacagagcattccaaagaatcattggagtgaggtacagaatgccaagtattccgcacgcatgtt
agctcagccaactgctagttcatcagtcaggcaaagtgcattcggagaatctctcagcatgatgtcgacgcacatggctttttactcgcatg
gcgtttctattattggtccgactaaaccgtttacgagatgatgaaccgttgatgcttccctgtcgaagcaggaccttgtctttgtcttttgtctcttgggccaatcactga
cctcccaacgcccgactaaaccgtttacgagatgatgaaccgttgatgcttccctgtcgaagcaggaccttgtcttttgtcttgtctcttgtct
tgcatgaaattcggcagcgtcccggaacggttcagatctaagctacgtgaccttttctcagctagtagtacccttagtactaaatagtattttgaggtattggcagc
cttcatgtggcacattccagcttcagcttggcaactgctcttccagcaattgtgccagtgattggtgaatgatccgatcatacctgccattagccgaaccgaat
aaatctattcagcttgtacctgtgaagcttgtacttgtaccttgtctctctccacctctgattctgccgtctctcctccaccctgtacctttcctcatcatctcaagtctac
gcaaggcgtgtacctgtcctccccatcacgccgcatgatggcctccagtttgtttctatctcgcaaccagctcagaagcaatgaatcactctctcttcttttctcc
cgaaccgccagctcccccatcacgccgcatgatggcctccagtttgttctatctcgcaaccagctcagaagcaatgaatcactctctcttcttctcc
ccttgccttcttatgctcagctttcacgccctccagtcagctcgcctctccacccacctaggttcgccatcgtcacaccctaggttcatctccatgcctccatagcctctcctctcccacgcc
accaaccaccaccaccaccaggccatgtaggatttctccgttcgtggcctcagcctcgtcagcctcgacacaccccagattcccagaggcggatga
agcagaagcagcaaggccatgtaggatttctccgttcgtggcctcagcctcgtcagcctcgacacaccccagattcccagaggcggatga
tccgcaccttaggctaatctctattcactgatccgtcttggcttggggggcctggtccccggccattgtggccaggccagtgcgacgcacgacgccgc
ggcggaccacaatcctccggcctgcttcaccgcacgcgtgtgagcgcagcagcgcagcgcggaaacgtgcaaggatggcaaaggcgggaaaggaggcacaacggccgtataagcgca
cgtcgcccgctgagtcctgccgctgcttcctctgcagcttcgcgcgttcacctgctgttcgcgcccgtgttcggccccatttcctgcgaaactcagctcagctgcttgaccaact
gatgctgccaggccttcattcgtcgtgcaagacgcggacgagacacgagcagatagacataaaagcgtagcaccccctgcatccagactgcaacctgcaacctcacctttttccctctt
aggatcacacgcggcaaggcggaaggaacgagacacgagatagacataaaagcgtagcaccccctgcatccagactgcaacctgcaacctcacctttttccctctt
ctcctccacccatcacaactcgccagtccctgactccttcacctcagaagaaagggcgttttgtgcagcaattgctttcctttccttcaacgctgc
ctccccgactgaagcgctgtctgtctgccagaggctagagattaccccgtaaca
```

Three nucleotides that were not present in the cloned version of the stp1 promoter are underlined.
Potential binding sites for regulatory proteins involved in transcription initiation are shown in bold.

*FIG. 3A*

SEQ ID NO:2

ATGGGCGAGAAAGAAGACATTCACGCTCACGAGAGCTCGACCATGTAAGTCAATTTGCCCAATGATCATTTTACTTCCCCTCTCT
TGTTTTGCCACCTCGCTTGGAGGAGTGAGTCTGCTTACACCATCTTCTCTGTTTTGCCTGAGTAGGGAGAGATCAGGACCAAGGTCGTG
ACCGGACACGAGGCCTTTGAGGAGGCCATGATGAAGGAGCCGCTCGCTGCTCATCAACAACCTGCTGGACCAAGGCTCAGTCCTCGTCTACAGCTTCTCCATC
ATTGCCTTCTTTCTGCAGCACCATCTGGGCCGGCATCTGGGCGCATCTGGGCCATTGTGTCTTCCATGTACCAGATTGGTGGTCGTCGCCCTTGTCGGCCTGCCATT
GTGGGAAACGACGGCATCTGGGCCGGCATCTGGGCCATTGTGTCTTCCATGTACCAGATTGGTGGTCGTCGCCCTTGTCGGCCTGCCATT
GACGGCTTTGGCCGCCGAATCGGCATGCTGTTGGGTGCCATCCTCATTGTCGTCGGCACCATCATCCAGGGTCTGTCAAACTCGCAGGGC
CAGTTCATGGGCGGCCGCGCTTTCTGCTTGGATTCGGCGTCTCCATTGCAGCGGCAGCGGGCCCATGTACGTGGTTGAGATTAACCACCCT
GCATACCGTGGACGCGTGGACGCGTAAGTATCCATTGCATGGAAGCATCTGCACCCGATGCTCAAGTTCACCCGATGCTCAAGTATGGAATCAATAGACTAACTTT
AGGAAGGGAGACAGTGGGAGGAAATGGACAGAAGACATCAAGCTTCACCCGATGCTCAAGTTCACCCGATGCTCAAGTATGGAATCAATAGACTAACTTT
CTTCTTCCCGTCCCTAGCCATGTACAACACTCTCTGGTTCTCGGGTGCCATCATCTCGGCCGGTGCCGCTCGAGGCGGCCTCAACGTCG
GAGGCGACTACTCGTGGCGACTCTTCGAGTATGAGCAGTCTCCTCACACCATCCGGCCCTTCTCCAGGCCCCTTCTCGCCCTCTTCTCGCATGTTCCTGCCGAGTCCC
CCCGCTGGCTCTACGTGCCACCACAGAAGGACGCAGCTCCAAGTCATCATGGCAGCGGCTGGTGGCAATGCGTTCTTCCTTACTTCCTCGGCT
TCCAGCTCCAGTCCGTCTGTGTGCAACGCGCTCAACATGAGCAGTCTCCTCACACCATTTGCCAGTGGGCTGGCAATGCGTTCTTCCTTACTTCCTCGGCT
GCGCCGCCGTCTACCGTCGTGTGCAACGCGCTCAACATGAGCAGTCTCCTCACACCATTTGCCAGTGGGCTGGCAATGCGTTCTTCCTTACTTCCTCGGCT
CCGTCCTCGATACGGCCCGGCGTCGTCACCGGCACCATTGCGCCCCCTTGCTGCCCTTCCTTTGCTGCACCGTGGCTCTGGGCTGCTGGGCATGACGG
TGGGGCGCCTTCCTGCTGTCGACCGGCGTTGGTCGTCGGACCAGCGTGGTCGTCGTCGACCGTGGCTCTGGGCTGCTGGGCATGACGG
TTGCCTCATCCGAATTTGCGCAGTCGTTCATCGGAAATGACGCCAATCCCAGCGATCCACACCGCTTCCAAGCGCTCCAAGGCTGCCC
TGGCCATGATCTTCATCTTTGGCCGTCTACTCTGTGGGCATCACTCCTCGCAGGCCCGTATCCCGTGAGGTGCTCTCCTTTGAGA
TGCGCGCCAAGGGCATGCCTTTGCCACCAACAGCGCTGCTGGACTCCTGAACCAGTTGCAACCAGTTGCATGGCCCGTGTCATGGACAAGA
TTGGCTGAAGACGTACATTATCCATCTTGGATCTCGTGCGTTGTCGTTCGTCATCATCCGAAGTTTCATTCCCGAGACCAAGGACGCA
CTGTAAGTGTTGCCAACTCACATTATCTCAACCATCCTTTTCAACCATCCTTTTCTACAGTTGGAAGAGCTTGACGAAATCTT
CGAGGCCAAGAACCCGGTCAAGACGTCAAGACGTCAAGACGTCAAGACGCGCGACAGCAGCAGCAGCACCGGCCACATTGTCAATATGCGAAGGCTTA
A

FIG. 3B

SEQ ID NO:3

ATGGGGCGAGAAAGAAGAGACATTCACGCTCTCACGAGGAGCTCAGGAGAGATCAGGACCAAGGTCGTGTGACCGGACGAGAGCCTTTGAGGAGGC
CATGATGAAGGAGGCCCGCCAAGGCCTGGACCAAGGCTCAGGTGCTCCAGCTGCCTTCTTCCATCATTGCCTTCTGCAGCACGAGGCCATGAACGGCT
ACGACGGCTCGCTCATCAACGCTCTGCTGCAGAACCCCTGGTTCAAGGCCAAGTACACTGTGGGAAACGACGGCATCTGGGCCGGCATTGTGTCT
TCCATGTACCAGATTGGTGTGGTCGTGGCCCTGCCATTGACGGCTTTGGCCGCGAATCGGCATGCTGTTGGGTGCCAT
CCTCATTGTCGTCGGCACCATCATCGCAGGTCTCGTCAAACTCGCAGGCCAGTTCATGGGCGGCCGTTTCTGCTTGCTGGGATTCGGCGTCTCATTG
CAGCGGCAGCGGGCCCCATGTACGTGGTGAGATTAACACCCTGAGCATACCGTGGACGCGTTGGCGACTACTCGTGCACCACAAGAAGACGCCGCGCCAAGGCTGTGCTCACCAAGT
CCCTCATCATCTCGACATGTCCCTGCCCGAGTCCCCGCAGCTCCAGCTGCTCTTCGAGTATGACATGAGCAGCTCCTCAACATGAGCAGCTGCCCGATAAGCGCTGG
ATCATGGCAACGGCGAAACCCCGACTCCGTCGGCTCGCGCCGCCAGCTCCTGCTTTGTGCAACGTCACCATTTTTGGCCAGTGGGCTGGCAATGC
TGGGATTACCGGGCGCTCTTCCCTCCGGCTCCATCCGCGATACGGCGGCGTTGGTCGTGCCGATCGGCAGTGCTCGGCGTCATACAGCTGCCAGC
GGTTCTTTTCCTACTTCCTCGGCCATTCTGGGCGCTGCCATCGGAATTGCCGCAGTGCAAGGCTACACCATCTCCTTTGCGGTGAACATGCACTGCTGG
AGTTCGCCTGGCATGACGGTTGCCCTCATCCATGATCTTCATCTTTTGGTGCCCAGCTTTCTGCAGGCCATGGCTCATCTCCTGTATCCGTCCAGCCTTTG
CTGGGATGACGGTTGCCCCATGATCTTCATCTTTTGGTGCCCAGCTTTCTGCATGGCCATCAGTTGCATGGCCCGTGTCATGGACGACAAGATT
AGATGCGCGCAAGGGCATGCCTCGAAGACGGTTGTCCGTCCAGACGGTTGTCGTCCTACTTTTTCATTCCCGAGACCAAGGGACGCACTTGA
GGCTGGAAGAGTACATTATCTTTACCATCTGGGATCTCGTCCAGACGCTCGCCGAAGACGCTGGGACGACGTCATGTCATGCCCGAGACCAAGGGACGCACTTGA
AGAGCTTGACGAGAAATCTTCGAGGCCAAGAACCCGGTCAAGACCTCAAGACGTCGACGACGAAGACCCGGTCGACGCCACGGCGACATTGTCAATA
TCGAGAAGGCTTAA

SEQ ID NO:4

MKEPPKAWTKAQVLVYSFSIIAFFCSTMNGYDGSLINNLLQNPWFKAKYTVGNDGIWAGIVSSMYQIGGVVALPFVGPAIDGFGRRIGMLLGAIL
IVVGTIIQGLSNSQGQFMGGRFLLGFGVSIAAAAGPMYVVEINHPAYRGRVGAMYNTLWFSGAIISAGAARGGLNVGGDYSWRLITWLQALFSGL
IIIFCMFLPESPRWLYVHHKKDAAKAVLTKYHGNGNPDSVWVQLQLFEYEQLLNMDGADKRWDYRALFRSRAAVYRLLCNVTITIFGQWAGNAV
LSYFLGSVLDTAGYTGTIAQANITLINNCQQFAWAILGAFLVDRVGRRPLLLFSFAACTVVWLGMTVASSEFAQSFIGNDANGDPIYSNPSASKA
ALAMIFIFGAVYSVGITPLQALYPVEVLSFEMRAKGMAFSSFATNAAGLLNQFAWPVSMDKIGWKTYIIFTIWDLVQTVVYFFIPETKGRTLEE
LDEIFEAKNPVKTSTTKKAVDSHGDIVNIEKA

FIG. 3C

TRICHODERMA PROMOTER

CROSS-REFERENCE TO RELATED APPLICATIONS

This application is a divisional of U.S. patent application Ser. No. 12/193,614, filed Aug. 18, 2008, now U.S. Pat. No. 8,044,192, issued Oct. 25, 2011, which claims priority to U.S. Provisional Application No. 60/971,807 filed Sep. 12, 2007, both of which are incorporated herein by reference.

FIELD OF THE INVENTION

A promoter for use in producing proteins in filamentous fungal host cells is provided. In one embodiment, the promoter comprises SEQ ID NO:1, or a variant of SEQ ID NO:1 or a truncated form thereof that has promoter activity in a host cell. Also provided are recombinant nucleic acids and vectors containing the promoter, and host cells containing a recombinant nucleic acid or vector. Methods of producing a protein using the host cells are also provided.

BACKGROUND OF THE INVENTION

Molecular biotechnology is a discipline that is based on the ability of researchers to transfer specific units of genetic information from one organism to another with the goal of producing commercially relevant amounts of useful products. One of the goals of this cloning process is to achieve maximum expression of the cloned gene. Recombinant production of a product encoded by a gene is accomplished by constructing expression vectors suitable for use in a host cell in which the nucleic acid coding for a desired product is placed under the expression control of a promoter. The expression vector is introduced into a host cell by various techniques, such as transformation, and production of the desired product is then achieved by culturing the transformed host cell under suitable conditions necessary for the functioning of the promoter included in the expression vector.

SUMMARY OF THE INVENTION

A promoter for use in producing proteins in a host cell is provided. In one embodiment, the promoter comprises SEQ ID NO:1 or a variant or truncated form thereof that has promoter activity in the host cell. Also provided are recombinant nucleic acids and vectors containing the promoter, and host cells containing a recombinant nucleic acid or vector. Methods of producing a protein using the host cells are also provided.

In certain cases, the promoter may be employed in filamentous fungal cells to express a protein. In some embodiments, the subject promoter is active in growth media containing glucose as a sole carbon source. As such, in certain cases, the promoter may be active in a growth medium that does not contain cellulose, lactose, sophorose, cellobiose, or other sugars or cellulose-related material that are known to induce activity of cellulase gene expression (see, e.g., Ilmen et al, Applied and Environmental Microbiology 1997 63: 1298-1306), although such inducers may be present in addition to glucose. In addition, the subject promoter may, in certain cases, be highly active at 37° C., as well as lower temperatures (e.g., 30° C.).

In certain embodiments, the promoter may comprise the nucleotide sequence of: a) SEQ ID NO: 1; b) a subsequence of SEQ ID NO: 1 that retains promoter activity; or c) a nucleic acid sequence that hybridizes under stringent hybridization conditions with SEQ ID NO: 1, or a subsequence thereof. In particular embodiments, the nucleotide sequence may be at least 80% identical (e.g., at least 90%, at least 95%, at least 98%, or at least 99% identical) to the nucleotide sequence of SEQ ID NO:1. In certain cases, the promoter may by identified by hybridizing the promoter of SEQ ID NO:1 with nucleic acid of a different species. In other cases, the promoter may be identified as being upstream of a nucleic acid that hybridizes to the coding sequence of SEQ ID NO:2. Hybridization may be done in solution or in silico (by BLAST, etc), for example.

A recombinant nucleic acid comprising the subject promoter is also provided. In certain cases, the recombinant nucleic acid may comprise a subject promoter and a polynucleotide, where the promoter and the polynucleotide are operably linked such that the promoter causes transcription of the polynucleotide in a cell. In certain cases, the polynucleotide may contain a coding sequence for a protein. The protein may be an enzyme, a reporter or a therapeutic protein (e.g., an antibody protein), for example. In certain embodiments, the protein may be a fusion protein which may, in certain cases, contain a signal sequence or carrier portion for secretion of the protein.

A nucleic acid vector comprising the subject recombinant nucleic acid is also provided, as well as a host cell containing the same. In certain embodiments, the recombinant nucleic acid may be present in the genome of the host cell or, in other embodiments, the recombinant nucleic acid may be present in a vector that replicates in the cell. The host cell may be any of a variety of different host cells, including *Trichoderma* sp, *Aspergillus* sp., *Penicillium* sp., *Neurospora* sp., *E. coli, Bacillus* sp., *Streptomyces* sp. and *Fusarium* sp. host cells. In one embodiment, the host cell may be a filamentous fungal host cell.

A culture of cells comprising culture medium and a subject host cell is also provided.

A method of producing a protein is also provided. In general terms, this method includes maintaining a subject culture of cells under conditions suitable to produce the protein. This method may further include recovering the protein from culture medium.

BRIEF DESCRIPTION OF THE FIGURES

FIGS. 3A, 3B and 3C show the nucleotide sequences of SEQ ID NOS:1, 2 and 3, and the amino acid sequence of SEQ ID NO:4. The three underlined nucleotides in SEQ ID NO:1 are not present in the stp1 promoter amplified from *T. reesei*. The sequences shown in bold are potential transcription factor binding sites.

DETAILED DESCRIPTION

Definitions

Figure 1:
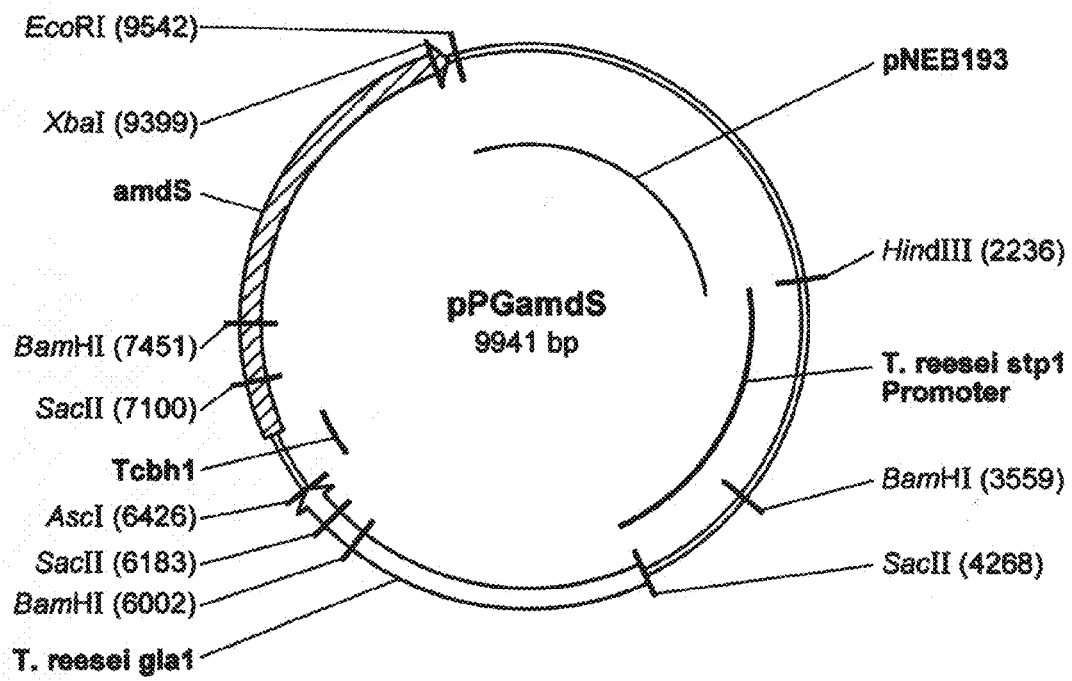
FIG. 1 is a schematic drawing of the plasmid pPGamdS.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with general dictionaries of many of the terms used in this invention. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

The term "promoter" is defined herein as a nucleic acid that directs transcription of a downstream polynucleotide in a cell. In certain cases, the polynucleotide may contain a coding sequence and the promoter may direct the transcription of the coding sequence into translatable RNA.

The term "promoter activity" is defined herein as the ability of a nucleic acid to direct transcription of a downstream polynucleotide in a host cell. To test promoter activity, the nucleic acid may be operably linked to a polynucleotide to produce a recombinant nucleic acid. The recombinant nucleic acid may be transferred into a cell and transcription of the polynucleotide may be evaluated. In certain cases, the polynucleotide may encode a protein, and transcription of the polynucleotide can be evaluated by assessing production of the protein in the cell. As will be discussed in greater detail below, the host cell may be a filamentous fungal host cell, e.g., a T. reesei host cell.

The term "functional equivalent", with reference to a promoter, is defined herein as a promoter having a nucleic acid sequence comprising a substitution, deletion and/or insertion in one or more nucleotides of a parent promoter. The term "functionally equivalent promoter" includes naturally-occurring equivalents and in vitro generated equivalents. A functionally equivalent promoter need not have a promoter activity that is identical to a parent promoter. The functionally equivalent promoter may have more promoter activity, less promoter activity or the same promoter activity compared to the corresponding parent promoter. As used herein the term "variant" promoter is used interchangeability with functional equivalent promoter.

The term "hybrid promoter" as defined herein means parts of two or more promoters which are fused together resulting in a sequence which is a fusion of two or more promoters and having promoter activity which results in the transcription of a downstream polynucleotide.

The term "tandem promoter" is defined herein as two or more promoters each of which is operably linked to a coding sequence of interest.

The term "isolated" as defined herein means a compound, a protein, cell, nucleic acid sequence or amino acid that is removed from at least one component with which it is naturally associated.

The term "coding sequence" is defined herein as a nucleic acid that, when placed under the control of appropriate control sequences including a promoter, is transcribed into mRNA which can be translated into a polypeptide. A coding sequence may contain a single open reading frame, or several open reading frames separated by introns, for example. A coding sequence may be cDNA, genomic DNA, synthetic DNA or recombinant DNA, for example. A coding sequence generally starts at a start codon (e.g., ATG) and ends at a stop codon (e.g., UAA, UAG and UGA).

The term "recombinant" refers to a polynucleotide or polypeptide that does not naturally occur in a host cell. A recombinant molecule may contain two or more naturally occurring sequences that are linked together in a way that does not occur naturally.

The term "heterologous" refers to elements that are not normally associated with each other. For example, a heterologous protein is a protein that is not produced in a wild-type host cell, a heterologous promoter is a promoter that is not present in nucleic acid that is endogenous to a wild type host cell, and a promoter operably linked to a heterologous coding sequence is a promoter that is operably linked to a coding sequence that it is not usually operably linked to in a wild-type host cell.

The term "operably linked" refers to a juxtaposition, wherein elements are in an arrangement allowing them to be functionally related. For example, a promoter is operably linked to a coding sequence if it controls the transcription of the sequence, and a signal sequence is operably linked to a protein if the signal sequence directs the protein through the secretion system of a host cell.

The term "nucleic acid" encompasses DNA, RNA, single or doubled stranded and modification thereof. The terms "nucleic acid" and "polynucleotide" may be used interchangeability herein.

The term "DNA construct" as used herein means a nucleic acid sequence that comprises at least two DNA polynucleotide fragments.

As used herein, the term "reporter" refers to a protein that is easily detected and measured. In certain cases, a reporter may be optically detectable, e.g., fluorescent, luminescent or colorigenic.

The term "signal sequence" or "signal peptide" refers to a sequence of amino acids at the N-terminal portion of a protein, which facilitates the secretion of the mature form of the protein outside the cell. The mature form of the extracellular protein lacks the signal sequence which is cleaved off during the secretion process.

The term "vector" is defined herein as a polynucleotide designed to carry nucleic acid sequences to be introduced into one or more cell types. Vectors include cloning vectors, expression vectors, shuttle vectors, plasmids, phage or virus particles, DNA constructs, cassettes and the like. Expression vectors may include regulatory sequences such as promoters, signal sequences, a coding sequences and transcription terminators.

An "expression vector" as used herein means a DNA construct comprising a coding sequence that is operably linked to suitable control sequences capable of effecting expression of a protein in a suitable host. Such control sequences may include a promoter to effect transcription, an optional operator sequence to control transcription, a sequence encoding suitable ribosome binding sites on the mRNA, enhancers and sequences which control termination of transcription and translation.

As used herein, the terms "polypeptide" and "protein" are used interchangeably and include reference to a polymer of any number of amino acid residues. The terms apply to amino acid polymers in which one or more amino acid residue is an artificial chemical analog of a corresponding naturally occurring amino acid, as well as to naturally occurring amino acid polymers. The terms also apply to polymers containing conservative amino acid substitutions such that the polypeptide remains functional. "Peptides" are polypeptides having less than 50 amino acid residues.

A "host cell" is a cell that contains a subject recombinant nucleic acid, either in the genome of the host cell or in an extrachromosomal vector that replicates autonomously from the genome of the host cell. A host cell may be any cell type.

The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, glucans, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic.

A "non-pathogenic" filamentous fungi is a strain that is not pathogenic to humans.

"Transformation" means introducing DNA into a cell so that the DNA is maintained in the cell either as an extrachromosomal element or chromosomal integrant.

Promoters

In certain embodiments, a subject promoter comprises the nucleotide sequence of SEQ ID NO: 1, or a subsequence (sometimes referred herein as a truncated promoter) of SEQ ID NO:1 that retains promoter activity. The subsequence may contain at least about 100 nucleotides, at least about 200 nucleotides; at least about 250 nucleotides; at least about 300 nucleotides; at least about 400 nucleotides; at least about 450 nucleotides, at least about 450 nucleotides, at least about 500 nucleotides, at least about 550 nucleotides, at least about 600 nucleotides, at least about 650 nucleotides that are contiguous in SEQ ID NO:1, including the entire contiguous sequence of SEQ ID NO:1, or a variant thereof that retains promoter activity.

In one embodiment, the first about 1 kb of SEQ ID NO:1 is removed and the promoter still retains activity, including 1.05 kb, 1.1 kb, 1.2 kb, 1.3 kb, and 1.4 kb. In some embodiments, the truncated promoter includes at least the part of the promoter containing the putative transcription factor binding sites (see in bold in SEQ ID NO:1). In another embodiment, the truncated promoter contains at least the region from the start of the positive regulatory transcription factor binding sites through the transcription start site.

In certain embodiments, a functional equivalent promoter may include one or more changes (e.g., 1, 2, 3, 4, 5, 6, 7, 8, 9, more than 10, up to 20, 30, 40 or 50 or more changes) relative to the nucleotide sequence of SEQ ID NO: 1, where a change can be a deletion, substitution or insertion, for example. In one exemplary embodiment, the nucleotide sequence of the subject promoter may include one to five or one to twenty nucleotide differences relative to the nucleotide sequence of the SEQ ID NO:1. In one embodiment, the third transcription factor binding site of SEQ ID NO:1 (ctgggg) is mutated to remove any inhibitory activity. In further embodiments, the first and second transcription factor binding sites are conserved as potential positive regulatory regions.

In other embodiments, the promoter may include a nucleotide sequence that hybridizes under stringent hybridization conditions to a polynucleotide having the nucleotide sequence of SEQ ID NO: 1, where stringent hybridization conditions encompass low, medium, high and very high stringency hybridization conditions. In other embodiments, the promoter may include a nucleic acid sequence that is upstream from a coding sequence that hybridizes to the coding sequence of SEQ ID NO:2 or SEQ ID NO:3. In these embodiments, the coding sequence that hybridizes to the coding sequence of SEQ ID NO:2 or SEQ ID NO:3 can encode a protein that is a sugar transporter.

"Low-stringency" conditions refer to washing with a solution of 1×SSC/0.1% SDS at 20° C. for 15 minutes. "Medium-stringency" conditions refer to washing with a solution of 1×SSC/0.1% SDS at 65° C. for 60 minutes. "High-stringency" conditions refer to washing with a solution of 0.2× SSC/0.1% SDS at 65° C. for 10 minutes. "Very high-stringency" conditions refer to washing with a solution of 0.2× SSC/0.1% SDS at 65° C. for 60 minutes.

Hybridization methods are described in great detail in Sambrook et al., MOLECULAR CLONING: A LABORATORY MANUAL (2$^{nd}$ Ed., 1989 Cold Spring Harbor, N.Y.). In one exemplary hybridization assay, a DNA sample is electrophoresed through an agarose gel (for example, 0.8% agarose) so that of the DNA fragment can be visualized by ethidium bromide staining. The gel is then briefly rinsed in distilled $H_2O$ and subsequently depurinated in an appropriate solution (such as, for example, 0.25M HCl) with gentle shaking followed by denaturation for 30 minutes (in, for example, 0.4 M NaOH) with gentle shaking. A renaturation step may be included, in which the gel is placed in 1.5 M NaCl, 1MTris, pH 7.0 with gentle shaking for 30 minutes. The DNA is then transferred onto an appropriate positively charged membrane, for example, *Maximum Strength Nytran Plus* membrane (Schleicher & Schuell, Keene, N. H.), using a transfer solution (such as, for example, 6×SSC, i.e., 900 mM NaCl, 90 mM trisodium citrate). Once the transfer is complete, generally after about 2 hours, the membrane is rinsed in e.g., 2×SSC (300 mM NaCl, 30 mM trisodium citrate) and air dried at room temperature. The membrane may be prehybridized (for approximately 2 hours or more) in a suitable prehybridization solution (such as, for example, an aqueous solution containing per 100 mL: 20-50 mL formamide, 25 mL of 20×SSPE (1×SSPE=0.18 M NaCl, 1 mM EDTA, 10 mM $NaH_2PO_4$, pH 7.7), 2.5 mL of 20% SDS, and 1 mL of 10 mg/mL sheared herring sperm DNA). As would be known to one of skill in the art, the amount of formamide in the prehybridization solution may be varied depending on the nature of the reaction obtained according to routine methods. Thus, a lower amount of formamide may result in more complete hybridization in terms of identifying hybridizing molecules than the same procedure using a larger amount of formamide. On the other hand, a strong hybridization band may be more easily visually identified by using more formamide.

A DNA probe generally between 50 and 500 bases in length having at least 100 or 200 or more contiguous nucleotides of the nucleic acid of FIG. 1 may be isolated by electrophoresis in an agarose gel, the fragment excised from the gel, and recovered from the excised agarose. This purified fragment of DNA may be labeled (using, for example, the Megaprime labeling system according to the instructions of the manufacturer) to incorporate $P^{32}$ in the DNA. The labeled probe is denatured by heating to 95° C. for 5 minutes and immediately added to the membrane and prehybridization solution. The hybridization reaction should proceed for an appropriate time and under appropriate conditions, for example, for 18 hours at 37° C. with gentle shaking or rotating. The membrane is rinsed (for example, in 2×SSC/0.3% SDS) and then washed in an appropriate wash solution, as described above, with gentle agitation. Hybridization can be detected by autoradiography.

In another embodiment, a subject promoter may contain a contiguous nucleotide sequence that is at least 80%, at least 85%, at least 90%, at least 95%, at least 96%, at least 97%, at least 98% or at least 99% identical to SEQ ID NO: 1, or a subsequence thereof. In one embodiment, the subject promoter may contain a contiguous nucleotide sequence that is at least 95% identical to SEQ ID NO:1. In a further embodiment, the promoter may have 80% sequence identity to SEQ ID NO:1 (including 85%, 90%, 95%, 97% and 99%) and 100% identity in transcription factor binding sites 1 and 2.

The term "identity" in the context of two nucleic acid sequences refers to nucleotides residues in the two sequences that are the same when aligned for maximum correspondence, as measured using any of the following sequence comparison algorithms. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information available on the world wide web (www) ncbi.nlm.nih.gov. The BLAST algorithm performs a statistical analysis of the similarity between two sequences (see, e.g., Karlin & Altschul, *Proc. Nat'l. Acad. Sci. USA* 90:5873-5787 (1993)).

As noted in the Examples section below, the nucleic acid of SEQ ID NO:1 was obtained from *Trichoderma reesei*, a filamentous fungus. As would be readily apparent, variants of SEQ ID NO:1 that retain promoter activity can be identified by identifying sequences that are similar to SEQ ID NO:1 in other filamentous fungi. Since most or all of the genome sequences of other filamentous fungi, e.g., *Aspergillus* (e.g., *Aspergillus fumigatus*, *Aspergillus oryzae* (see, e.g., Machida et al, Nature 2005 438, 1157-1161), *Aspergillus nidulans*, *Aspergillus fumigatus*, *Aspergillus niger*, *Aspergillus flavus*, and *Aspergillus terreus*), *Neurospora* (e.g., *Neurospora crassa*), and *Fusarium* (e.g., *Fusarium graminearum*) are available, functional equivalents of SEQ ID NO:1 that have promoter activity may be readily identifiable. Such promoters should be linked to a polynucleotide encoding a sugar transporter, e.g., a protein having at least 80% identity to SEQ ID NO:4, including 85%, 90%, 95%, 97%, 99% and 100% identity.

As noted above, a subject promoter may have promoter activity in a host cell. Promoter activity may be detected using any suitable assay. In certain embodiments, a subject promoter may be operably linked to a polynucleotide, and transcription of the polynucleotide may be detecting using any suitable method, e.g., Northern blotting or RT-PCR, etc. In other embodiments, the promoter may be operably linked to a polynucleotide that encodes a protein, e.g., a reporter protein, and the activity of the promoter can be evaluated by detecting the protein. In these embodiments, if necessary, a 5' untranslated region may be linked to the promoter such that the resultant transcript has a 5' UTR followed by a coding sequence. As would be recognized, the results obtained from such an assay may be compared to results compared to a suitable control, e.g., a negative or positive control, to determine the significance of results obtained. Any host cell, e.g., a bacterial host cell such as *E. coli*, *Bacillus* or *Streptomyces* host cell, or a filamentous fungal cell, e.g., an *Aspergillus* ssp., *Trichoderma* ssp. or *Fusarium* ssp. host cell may be employed. There is no requirement for a subject promoter to be contained within a particular host cell. In certain cases, the promoter may be tested for promoter activity in a *Trichoderma reesei* host cell.

The activity of a subject promoter is generally detectable using the assay employed. In certain cases, the activity of a variant promoter (e.g., a functionally equivalent promoter) may have at least about 20%, at least about 30%, at least about 40%, at least about 50%, at least about 60%, at least about 80%, at least about 90%, at least about 95% or at least about 100% of the promoter activity of the promoter of SEQ ID NO: 1 in the same type of cell, e.g., a *Trichoderma* cell. In some cases, the activity of a variant promoter (e.g., functionally equivalent promoter) may be greater, for example more than about 100%, more than about 150%, more than about 200%, more than about 250%, or more than 1000% of the activity of SEQ ID NO: 1 in the same type of cell. In other embodiments, the promoter has at least about 40%, 50%, 60%, 70%, 80% 90% 95%, 97%, and 99% of the activity on a particular carbon source.

In certain embodiments, the promoter may be a hybrid promoter comprising a portion of a subject promoter and a portion of another promoter. In some embodiments, the hybrid promoter will include a subsequence of SEQ ID NO: 1 having at least about 100 nucleotides, at least about 150 nucleotides; at least about 200 nucleotide; at least about 250 nucleotides; at least about 300 nucleotides, at least about 350 nucleotides, at least about 400 nucleotides, at least about 500 nucleotides, at least about 550 nucleotides, at least about 600 nucleotides, at least about 650 nucleotides, at least about 700 nucleotides, at least about 750 nucleotides, at least about 800 nucleotides, at least about 850 nucleotides, at least about 900 nucleotides, at least about 950 nucleotides, at least about 1000 nucleotides, at least about 1050 nucleotides, at least about 1100 nucleotides, at least about 1150 nucleotides, at least about 1200 nucleotides, at least about 1250 nucleotides, at least about 1300 nucleotides, at least about 1350 nucleotides, at least about 1400 nucleotides, at least about 1450 nucleotides, at least about 1500 nucleotides, at least about 1550 nucleotides, at least about 1600 nucleotides, at least about 1650 nucleotides, at least about 1700 nucleotides, at least about 1750 nucleotides, at least about 1800 nucleotides, at least about 1850 nucleotides, and at least about 1900 nucleotides of SEQ ID NO: 1. In certain embodiments, the hybrid promoter will include a subsequence of SEQ ID NO:1 comprising the first and second transcription factor binding sites.

The other promoter of the hybrid promoter may be any promoter that shows promoter activity in a host cell, and includes mutant promoters, truncated promoters and the like which may or may not be native to the host cell. Examples of other promoters, which may be useful in a hybrid promoter of the invention, include fungal and bacterial promoters. Some specific nonlimiting examples include; the aprE promoter or a mutant aprE promoter (WO 01/51643); the aph promoter of the *Streptomyces fradiae* aminoglycoside 3'-phosphotransferase gene; an *Aspergillus niger* glucoamylase (glaA) promoter; the glucose isomerase (GI) promoter of *Actinoplanes missouriensis* and the derivative GI (GIT) promoter (U.S. Pat. No. 6,562,612 and EPA 351029); the glucose isomerase (GI) promoter from *Streptomyces lividans*, the short wild-type GI promoter, the 1.5 GI promoter, the 1.20 GI promoter, or any of the variant GI promoters as disclosed in WO 03/089621; the cbh1, cbh2, egl1 and egl2 promoters from filamentous fungi and specifically the *Trichoderma reesei* cellobiohydrolase I promoter (GenBank Accession No. D86235); the *Aspergillus* niger or *A. awamori* glucoamylase (glaA) promoter (Nunberg et al. (1984) supra, and Boel et al., (1984) supra); the lacZ and tac promoters (Bagdasarion et al., 1983, *Gene* 26:273-282); the ermE promoter (Ward et al., 1986, *Mol. Gen. Genet.* 203:468-478 and Schmitt-John et al., 1992, *Appl. Microbiol. Biotechnol.* 36:493-498); and the *Bacillus subtilis* phage ø29 promoters (Pulido et al., 1986, *Gene* 49:377-382). Promoters effective in *Streptomyces* are listed in Hopwood et al., (Hopwood et al., Regulation of Gene Expression in Antibiotic-producing *Streptomyces*. In Booth, I. and Higgins, C. (Eds) SYMPOSIUM OF THE SOCIETY FOR GENERAL MICROBIOLOGY, REGULATION OF GENE EXPRESSION, Cambridge University Press, 1986 pgs. 251-276). *Streptomyces* phage promoters are also disclosed in Labes et al., 1997, *Microbiol.* 143:1503-1512. Other promoters which may be effective for use in the hybrid promoters herein are promoters listed in Deuschle et al., 1986 *EMBO J.* 5:2987-2994 and WO 96/00787.

The promoter may also be a tandem promoter, which comprises two or more promoters. In some embodiments, the tandem promoter will include the subject promoter and one or more other promoters such as those discussed above for hybrid promoters.

Recombinant Nucleic Acids

A subject recombinant nucleic acid may comprise a subject promoter and a polynucleotide encoding a protein (i.e., a coding sequence), where the promoter and the polynucleotide are operably linked such that the isolated nucleic acid causes transcription of the polynucleotide, and, in certain embodiments, production of the protein.

The encoded protein may be an enzyme, a therapeutic protein, a reporter protein, a selectable marker, a food additive or a foodstuff or the like.

Enzyme usage in industrial applications covers a wide array of enzyme functionalities, for example industrial enzymes include oxidoreductases (e.g., glucose oxidases, catalases, and laccases), transferases (e.g. transglutaminases), hydrolases (e.g., lipases, phytases, amylases, cellulases, xylanases, mannanases, proteases, subtilisins, and aspergillopepsins), lyases (e.g. pectate lyases) and isomerases (e.g. xylose isomerases).

In one embodiment, the protein may be an enzyme such as a carbohydrase, such as a liquefying and saccharifying α-amylase, an alkaline α-amylase, a β-amylase, a cellulase; a dextranase, an α-glucosidase, an α-galactosidase, a glucoamylase, a hemicellulase, a pentosanase, a xylanase, an invertase, a lactase, a naringanase, a pectinase or a pullulanase; a protease such as an acid protease, an alkali protease, bromelain, ficin, a neutral protease, papain, pepsin, a peptidase, rennet, rennin, chymosin, subtilisin, thermolysin, an aspartic proteinase, or trypsin; a lipase or esterase, such as a triglyceridase, a phospholipase, acyl transferase, a pregastric esterase, a phosphatase, a phytase, an amidase, an iminoacylase, a glutaminase, a lysozyme, or a penicillin acylase; an isomerase such as glucose isomerase; an oxidoreductases, e.g., an amino acid oxidase, a catalase, a chloroperoxidase, a glucose oxidase, a hydroxysteroid dehydrogenase or a peroxidase; a lyase such as a acetolactate decarboxylase, an aspartic β-decarboxylase, a fumarese or a histadase; a transferase such as cyclodextrin glycosyltransferase; or a ligase, for example.

In particular embodiments, the protein may be an aminopeptidase, a carboxypeptidase, a chitinase, a cutinase, a deoxyribonuclease, an α-galactosidase, a β-galactosidase, a β-glucosidase, a laccase, a mannosidase, a mutanase, a pectinolytic enzyme, a polyphenoloxidase, ribonuclease or transglutaminase, for example.

In other particular embodiments, the enzyme will be a α-amylase, a cellulase; an α-glucosidase, an α-galactosidase, a glucoamylase, a hemicellulase, a xylanase, a pectinase, a pullulanase; an acid protease, an alkali protease, an aspartic proteinase, a lipase, a cutinase or a phytase.

In another embodiment, the protein may be a therapeutic protein (i.e., a protein having a therapeutic biological activity). Examples of suitable therapeutic proteins include: erythropoietin, cytokines such as interferon-α, interferon-β, interferon-γ, interferon-o, and granulocyte-CSF, GM-CSF, coagulation factors such as factor VIII, factor IX, and human protein C, antithrombin III, thrombin, soluble IgE receptor α-chain, IgG, IgG fragments, IgG fusions, IgM, IgA, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon like protein 1 and IL-2 receptor agonist. Antibody proteins, e.g., monoclonal antibodies that may be humanized, are of particular interest.

In a further embodiment, the protein may be a reporter protein. Such reporter proteins may be optically detectable or colorigenic, for example. In this embodiment, the protein may be a β-galactosidase (lacZ), β-glucuronidase (GUS), luciferase, alkaline phosphatase, nopaline synthase (NOS), chloramphenicol acetyltransferase (CAT), horseradish peroxidase (HRP) or a fluorescent protein green, e.g., green fluorescent protein (GFP), or a derivative thereof.

Examples of selectable markers include but are not limited to ones that confer antimicrobial resistance (e.g. resistance to hygromycin, bleomycin, chloramphenicol or phleomycin), and proteins that confer metabolic advantage, e.g., amdS, argB and pyr4. Selectable markers are further described in Kelley et al., (1985) EMBO J. 4: 475-479; Penttila et al., (1987) Gene 61:155-164 and Kinghorn et al (1992) Applied Molecular Genetics of Filamentous Fungi, Blackie Academic and Professional, Chapman and Hall, London.

In certain embodiments, the coding sequence may encode a fusion protein. In some of these embodiments, the fusion protein may provide for secretion of the protein from the host cell in which it is expressed and, as such, may contain a signal sequence operably linked to the N-terminus of the protein, where the signal sequence contains a sequence of amino acids that directs the protein to the secretory system of the host cell, resulting in secretion of the protein from the host cell into the medium in which the host cell is growing. The signal sequence is cleaved from the fusion protein prior to secretion of the protein. The signal sequence employed may be endogenous or non-endogenous to the host cell and, in certain embodiments, may be signal sequence of a protein that is known to be highly secreted from a host cell. In particular embodiments, the signal sequence protein may be any signal sequence that facilitates protein secretion from a filamentous fungal (e.g., *Trichoderma* or *Aspergillus*) host cell. Such signal sequences include, but are not limited to: the signal sequence of cellobiohydrolase I, cellobiohydrolase II, endoglucanase I, endoglucanase II, endoglucanase III, α-amylase, aspartyl proteases, glucoamylase, mannanase, glycosidase and barley endopeptidase B (see Saarelainen, Appl. Environ. Microbiol. 1997 63: 4938-4940), for example. Other of signal sequences are those originating from the α factor gene (yeasts e.g. *Saccharomyces, Kluyveromyces* and *Hansenula*) or the α amylase gene (*Bacillus*). In certain embodiments, therefore, the subject recombinant nucleic acid may comprise: a signal sequence-encoding nucleic acid operably linked to a protein-encoding nucleic acid, where translation of the nucleic acid in a host cell produces a fusion protein comprising a protein having an N-terminal signal sequence for secretion of the protein from the host cell.

In particular embodiments, the fusion protein may further contain a "carrier protein", which is a portion of a protein that is endogenous to and highly secreted by the host cell. Suitable carrier proteins include those of *T. reesei* mannanase I (Man5A, or MANI), *T. reesei* cellobiohydrolase II (Cel6A, or CBHII) (see, e.g., Paloheimo et al Appl. Environ. Microbiol. 2003 December; 69(12): 7073-7082) or *T. reesei* cellobiohydrolase I (CBHI). In one embodiment, the carrier protein is a truncated *T. reesei* CBH1 protein that includes the CBH1 core region and part of the CBH1 linker region. A fusion protein containing, from amino-terminus to carboxy-terminus, a signal sequence, a carrier protein and a subject protein in operable linkage is therefore provided, as well as a nucleic acid encoding the same.

In certain embodiments, the polynucleotide may be codon optimized for expression of the protein in a particular host cell. Since codon usage tables listing the usage of each codon in many cells are known in the art (see, e.g., Nakamura et al, Nucl. Acids Res. 2000 28: 292) or readily derivable, such nucleic acids can be readily designed giving the amino acid sequence of a protein to be expressed.

In addition to a coding sequence, the recombinant nucleic acid may in certain embodiments further contain other elements that are necessary for expression of the protein in the host cell. For example, the nucleic acid may contain a transcriptional terminator, and 5' and 3' UTR sequences. Suitable 5' UTR sequences may be obtained from the *T. reesei* cbh1, cbh2, egl1, egl2, egl5, xln1 and xln2 genes, for example. Suitable terminators include the *T. reesei* cbh1, cbh2, egl1, egl2, egl5, xln1 and xln2 terminators, and many others, including, for example, the terminators from *A. niger* or *A. awamori* glucoamylase genes (Nunberg et al. (1984) supra, and Boel et al., (1984) supra), *Aspergillus nidulans* anthranilate synthase genes, *Aspergillus oryzae* TAKA amylase genes, or *A. nidulans* trpC (Punt et al., (1987) Gene 56:117-124). The promoter and/or terminator may be native or non-endogenous to the host cell. In certain cases, the promoter and protein coding sequence may be separated by a sequence encoding a 5' untranslated region, for example.

As will be discussed in greater detail below, a subject recombinant nucleic acid may be present in a vector, or integrated into a genome (i.e., the nuclear genome) of a host cell.

Vectors

A subject recombinant nucleic acid may be present in a vector, e.g., a phage, plasmid, viral, or retroviral vector that autonomously replicates in a host cell. In certain embodiments, the vector may be an expression vector for expressing a protein in a host cell. In certain embodiments, the vector may be an expression vector for expressing a subject polypeptide in a filamentous fungal cell.

Vectors for expression of recombinant proteins are well known in the art (Ausubel, et al, Short Protocols in Molecular Biology, 3rd ed., Wiley & Sons, 1995; Sambrook, et al., Molecular Cloning: A Laboratory Manual, Second Edition, (1989) Cold Spring Harbor, N.Y.).

A subject vector may be constructed using well known techniques as is generally described for example in EPO publication 0 215 594. Once the fusion DNA construct is made it may be incorporated into any number of vectors as is known in the art. While the DNA construct will preferably include a promoter sequence, in some embodiments the vector will include regulatory sequences functional in the host to be transformed, such as promoters, ribosomal binding sites, transcription start and stop sequences, terminator sequences, polyadenylation signals, enhancers and or activators.

Terminator sequences which are recognized by the expression host to terminate transcription may be operably linked to the 3' end of the fusion DNA construct encoding the fusion protein to be expressed. Those of general skill in the art are well aware of various terminator sequences that may be used with filamentous fungi. Non-limiting examples include the terminator from the *Aspergillus nidulans* trpC gene (Yelton M. et al., (1984) Proc. Natl. Acad. Sci. USA 81: 1470-1474) the terminator from the *Aspergillus niger* glucoamylase genes (Nunberg et al. (1984) Mol. Cell. Biol. 4: 2306-2353).

In further embodiments, the fusion DNA construct or the vector comprising the fusion DNA construct will contain a selectable marker gene to allow the selection of transformed host cells. Selection marker genes are well known in the art and will vary with the host cell used. Examples of selectable markers include but are not limited to ones that confer antimicrobial resistance (e.g. hygromycin, bleomycin, chloroamphenicol and phleomycin). Sequences that confer metabolic advantage, such as nutritional selective markers also find use. Also, sequences encoding proteins that complement an auxotrophic defect may be used as selection markers (e.g. pyr4 complementation of a pyr4 deficient *A. nidulans*, *A. awamori* or *Trichoderma reesei* and argB complementation of an argB deficient strain). Reference is made to Kelley et al., (1985) EMBO J. 4: 475-479; Penttila et al., (1987) Gene 61:155-164 and Kinghorn et al (1992) Applied Molecular Genetics of Filamentous Fungi, Blackie Academic and Professional, Chapman and Hall, London.

In one embodiment, the vector is a *Trichoderma* expression vector related to pTrex3g, which is described in detail in Example 6 of WO 05/001036.

Host Cells

A host cell comprising a subject recombinant nucleic acid is also provided. The host cell may be any cell type, e.g., bacterial (such as *E. coli, Bacillus* sp. or *Streptomyces* sp.) or fungal (such as a non-filamentous or filamentous fungal) host cell. In certain embodiments, the host cell may be a filamentous fungal host cell. In some embodiments, the host cell may be a cell of a strain that has a history of use for production of proteins that has GRAS status, i.e., a Generally Recognized as Safe, by the FDA.

In particular embodiments, the subject host cell may be a fungal cell of the following species: *Trichoderma*, (e.g., *Trichoderma reesei* (previously classified as *T. longibrachiatum* and currently also known as *Hypocrea jecorina*), *Trichoderma viride, Trichoderma koningii,* and *Trichoderma harzianum*)); *Penicillium* sp., *Humicola* sp. (e.g., *Humicola insolens* and *Humicola grisea*); *Chrysosporium* sp. (e.g., *C. lucknowense*), *Gliocladium* sp., *Aspergillus* sp. (e.g., *Aspergillus oryzae, Aspergillus niger, Aspergillus nidulans, Aspergillus kawachi, Aspergillus aculeatus, Aspergillus japonicus, Aspergillus sojae,* and *Aspergillus awamori*), *Fusarium* sp., *Humicola* sp., *Mucor* sp., *Neurospora* sp., *Hypocrea* sp., or *Emericella* sp. (See also, Innis et al., (1985) Sci. 228:21-26), among others. Other host cells include *Bacillus* sp., including, but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis,* and *Steptomyces* sp., including, but not limited to: *S. lividans, S. carbophilus* and *S. helvaticus*.

In some embodiments, subject fungal host cells may be of a strain of *Aspergillus niger* which include ATCC 22342, ATCC 44733, ATCC 14331, ATCC 11490, NRRL 3112, and strains derived therefrom. In some embodiments, subject fungal cells may be strains of *Trichoderma* which include functional equivalents of RL-P37 (Sheir-Neiss et al. (1984) Appl. Microbiol. Biotechnology 20:46-53). Other useful host strains include; NRRL 15709, ATCC 13631, ATCC 26921 (QM 9414) ATCC 32098, ATCC 32086, and ATCC 56765 (RUT-30).

In some embodiments, a host cell may be one wherein native genes have been deleted or inactivated. For example genes corresponding to protease genes (e.g. aspartyl protease) (Berka et al. (1990) Gene 86:153-162 and U.S. Pat. No. 6,509,171 or genes corresponding to cellulase genes may be deleted or inactivated, (e.g. cbh1, cbh2 and egl1, and egl2) such as the quad deleted strain of *T. reesei* disclosed in WO 05/001036.

The above described fusion DNA construct may be present in the nuclear genome of the host cell or may be present in a plasmid that replicates in the host cell, for example.

Introduction of a nucleic acid into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (See, e.g., Ausubel et al., (1987), supra, chapter 9; and Sambrook (1989) supra, and Campbell et al., (1989) *Curr. Genet.* 16:53-56). Reference is also made to WO 05/001036; U.S. Pat. No. 6,022,725; U.S. Pat. No. 6,103,490; U.S. Pat. No. 6,268,328; and published U.S. patent applications 20060041113, 20060040353, 20060040353 and 20050208623, which publications are incorporated herein by reference.

The expression of recombinantly introduced proteins in *Trichoderma* is described in U.S. Pat. No. 6,022,725; U.S. Pat. No. 6,268,328; Harkki et al. (1991); *Enzyme Microb. Technol.* 13:227-233; Harkki et al., (1989) *Bio Technol.* 7:596-603; EP 244,234; EP 215,594; and Nevalainen et al., "The Molecular Biology of Trichoderma and its Application to the Expression of Both Homologous and Heterologous Genes", in MOLECULAR INDUSTRIAL MYCOLOGY, Eds. Leong and Berka, Marcel Dekker Inc., NY (1992) pp. 129-148). Reference is also made to Cao et al., (2000) Protein Sci. 9:991-1001; Yelton et al., (1984) Proc. Natl. Acad. Sci. 81:1470-1471; U.S. Pat. No. 6,590,078; and Berka, et al., (1991) in: Applications of Enzyme Biotechnology, Eds. Kelly and Baldwin, Plenum Press, NY) for transformation of *Aspergillus* strains.

In one embodiment, the preparation of *Trichoderma* sp. for transformation involves the preparation of protoplasts from fungal mycelia. (See, Campbell et al., (1989) *Curr. Genet.* 16:53-56). In some embodiments, the mycelia are obtained from germinated vegetative spores. Transformation and protein expression in *Aspergillus* and *Trichoderma* is further described in, for example U.S. Pat. No. 5,364,770; U.S. Pat. No. 6,022,725; and Nevalainen et al., 1992, The Molecular Biology of *Trichoderma* and its Application to the Expression of Both Homologous and Heterologous Genes, in MOLECULAR INDUSTRIAL MYCOLOGY, Eds. Leon and Berka, Marcel Dekker, Inc. pp. 129-148.

A culture of cells is also provided. The culture of cells may contain a population of the above-described cells, and growth medium. The growth medium may contain glucose as a carbon source. In particular embodiments, glucose may be the sole carbon source of the growth medium. The growth medium may be free of a carbon source that is known to induce activity of cellulase gene expression (see, e.g., Ilmen et al, Applied and Environmental Microbiology 1997 63: 1298-1306). For example, the growth medium may be free of cellulose, lactose, sophorose, cellobiose, and/or other sugar or cellulose-related material that induce cellulase expression. The culture of cells may be at a temperature of about 30° C. (e.g., 27-33° C.), or at a temperature of about 37° C. (e.g., 34-39° C.), for example. In a particular embodiment, the growth medium may contain glucose, glucose and sopohorose, or lactose as a carbon source, and the culture may be grown at 30° C. or 37° C.

Protein Production

Methods of using the above-described cells are also provided. The proteins produced by the cells may be employed in a variety of methods.

In certain embodiments, the subject methods include: culturing the cells to produce a recombinant protein. In certain embodiments and as discussed above, the protein may be secreted into the culture medium. As such, certain embodiments of the method include the step of recovering the protein from the culture medium.

Cells may cultured in a standard medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth also find use in the present invention. Preferred culture conditions for a given filamentous fungus are known in the art and may be found in the scientific literature and/or from the source of the fungi such as the American Type Culture Collection (ATCC) and Fungal Genetics Stock Center.

In some embodiments, a subject host cell may be cultured under batch or continuous fermentation conditions. A classical batch fermentation is a closed system, wherein the composition of the medium is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase and finally to a stationary phase where growth rate is diminished or halted. If untreated, cells in the stationary phase eventually die. In general, cells in log phase are responsible for the bulk of production of end product.

A variation on the standard batch system is the "fed-batch fermentation" system, which also finds use with the present invention. In this variation of a typical batch system, the substrate is added in increments as the fermentation progresses. Fed-batch systems are useful when catabolite repression is apt to inhibit the metabolism of the cells and where it is desirable to have limited amounts of substrate in the medium. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and known in the art.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are known.

A fungal host cell may be cultured in a standard medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) Appl. Environ. Microbiol. 63:1298-1306). Common commercially prepared media (e.g., Yeast Malt Extract (YM) broth, Luria Bertani (LB) broth and Sabouraud Dextrose (SD) broth also find use in the present methods. Preferred culture conditions for fungal host cells are known in the art and may be found in the scientific literature and/or from the source of the fungi such as the American Type Culture Collection (ATCC) and Fungal Genetics Stock Center.

Protein may be recovered from growth media by any convenient method, e.g., by precipitation, centrifugation, affinity, filtration or any other method known in the art. In another embodiment, a culture of cells is provided, where the culture of cells comprises: a) growth medium and b) the above-described host cell.

As noted above, the cells may be grown using glucose as a carbon source which, in certain embodiments, may be the sole carbon source for the cells. The growth medium may be free of cellulose, lactose, sophorose, cellobiose, and/or other sugar or cellulose-related material that induce cellulase expression. The cells may be cultured at a temperature of about 30° C. (e.g., 27-33° C.), or at a temperature of about 37° C. (e.g., 34-39° C.), for example.

In order to further illustrate the present invention and advantages thereof, the following specific examples are given with the understanding that they are being offered to illustrate the present invention and should not be construed in any way as limiting its scope.

EXAMPLE 1

Identification of the *Trichoderma reesei* stp1 Gene

The stp1 gene was identified from the *Trichoderma reesei* genome sequence data made publicly available by the United States Department of Energy Joint Genome Institute (JGI) and accessible at the website genome.jgi-psf.org/Trire2/Trire2.home. Several gene models that annotated the gene with the translation start and stop codons and introns were proposed by JGI. Manual inspection of these models suggests that the model labeled estExt_fgenesh1_pg.C_30027, associated with the Protein ID 43977, is the most likely to be correct. All of the elements (transcription factor binding sites, transcription start site, etc.) of the promoter for this gene are expected to reside within approximately 2 kb sequence that is immediately upstream, or 5', of the translation initiation codon. The sequence of this 2 kb promoter region as extracted from the JGI genome data is shown as SEQ ID NO:1. However, it is likely that the promoter will still be active with the removal of at least the first 1 kb (or more) of SEQ ID NO:1. Further, 3 possible transcription factor binding sites (regulatory sites) were identified and are shown in FIG. 3 in SEQ ID NO:1 in bold. The site closest to the transcription start site (Site 3) is a potential repressor binding region. The other sites (Site 1 and 2) are positive regulatory sites.

The sequence of the open reading frame of the stp1 gene, including introns, is shown as SEQ ID NO:2 and the open reading frame with three predicted introns removed is shown as SEQ ID NO:3. The deduced amino acid sequence of the encoded STP1 protein is shown as SEQ ID NO:4.

The STP1 protein sequence has similarity with sugar transporter proteins of the major facilitator superfamily. Twelve transmembrane regions are predicted by topology prediction algorithms such as TMHMM (website: cbs.dtu.dk/services/TMHMM-2.0/) and Prosite motifs corresponding to sugar transport proteins can be recognized within the amino acid sequence (website expasy.org/prosite/).

Expression of the stp1 gene in different *T. reesei* strains and during growth under a variety of conditions was investigated by examining data from transcript profiling experiments using microarrays (e.g., Foreman et al., 2003, J. Biol. Chem. 278:31988-31997). These data suggested that the stp1 gene is highly expressed under conditions that are known to induce cellulase and hemicellulase production in *Trichoderma reesei* such as growth in the presence of cellulose or lactose or as a result of induction by sophorose. Expression of stp1 is low when abundant glucose is present as the carbon source. However, unlike cellulase gene expression, stp1 expression is increases dramatically at the point when glucose is exhausted from the medium. These features of stp1 gene regulation made the stp1 promoter attractive for directing expression of genes encoding desired proteins in *Trichoderma reesei*.

EXAMPLE 2

Construction of a Vector for Expression of the Trichoderma reesei Glucoamylase Gene Using the stp1 Promoter A vector, pPGamdS, was designed for the expression of an open reading frame encoding the *T. reesei* glucoamylase. The promoter region from the stp1 gene was amplified by PCR using the following primer pair.

```
Primer newpF:
                                        (SEQ ID NO: 5)
5'-ggccaagcttgagctgagtgtcaaggcagttgcac Primer newpR:
                                        (SEQ ID NO: 6)
5'-gggaccgcggtaatctctagcctctgggccagagac
```

These primers were designed to amplify the stp1 promoter and introduce a HindIII restriction site at the 5' and a SacII cleavage site at the 3' end seven nucleotides upstream from the translation start codon. The template for the PCR reaction was genomic DNA isolated from *Trichoderma reesei*. Pfu Turbo DNA polymerase (Stratagene Corp.) was used according to the manufacturer's instructions. The following temperatures and times were used for the thermocycling steps of the PCR. 95° C. for 30 seconds; followed by 30 cycles of 95° C. for 30 seconds, 55° C. for 30 seconds and 68° C. for 2 minutes; and a final step of 68° C. for 7 minutes. An approximately 2 kb DNA fragment was obtained and was cloned into plasmid pCR-BluntII-TOPO (InVitrogen Life Technologies) according to the supplier's instructions. DNA sequence analysis confirmed that the stp1 promoter had been cloned. Except for the absence of three base pairs in the DNA sequence of the cloned stp1 promoter, the sequence was identical to that in the JGI *Trichoderma reesei* database. The nucleotide positions are 1278, 1279 and 1280, relative to SEQ ID NO:1.

The cloned stp1 promoter was next fused to an open reading frame encoding the *Trichoderma reesei* glucoamylase using a PCR fusion strategy. The DNA sequence and the polypeptide sequence of the *Trichoderma reesei* glucoamylase is disclosed in WO 06/060062 published Jun. 6, 2006 and reference is made to SEQ ID NO:1, SEQ ID NO:2 and SEQ ID NO: 4 therein.

The cloned stp1 promoter was first amplified from pCR-BluntII-TOPO using the following primer pair.
Primer newpF and

```
Primer PGfuse1-r:
                                        (SEQ ID NO: 7)
5'-gtcgacaggacgtgcattgttaccgcggtaatctctagcctctg
```

The *Trichoderma reesei* gla1 open reading frame (approximately 2 kb in length), encoding glucoamylase, was amplified using the following primer pair.

```
Primer PGfuse1:
                                        (SEQ ID NO: 8)
5'-cagaggctagagattaccgcggtaacaatgcacgtcctgtcgac Primer trgaR:
                                        (SEQ ID NO: 9)
5'-cgcggcgcgccttacgactgccaggtgtcctccttg
```

The products from the above two amplification reactions were mixed and served as template in a subsequent reaction using the following primer pair.
Primer newpF and Primer trgaR The approximately 4 kb product from this amplification reaction was a fragment of DNA consisting of the stp1 promoter linked to the gla1 coding region and having a HindIII restriction site at the 5' end and an AscI restriction site at the 3' end. This 4 kb DNA fragment was cloned into pCR-BluntII-TOPO and was subsequently excised as a HindIII-AscI fragment for insertion into a *Trichoderma* expression vector to create pPGamdS (FIG. 1).

In pPGamdS the *T. reesei* glucoamylase open reading frame is flanked by the stp1 promoter and the *T. reesei* cbh1 gene terminator sequences. The vector is based on the bacterial plasmid pNEB193 (New England Biolabs) and also contains the *Aspergillus nidulans* amdS gene, encoding acetamidase, with its native promoter and terminator sequences for use as a selectable marker for transformation of *T. reesei*.

Plasmid pPGamdS was inserted into a *Trichoderma reesei* strain derived from RL-P37 (Sheir-Neiss, G. and Montenecourt, B. S., 1984, Appl. Microbiol. Biotechnol. 20:46-53) and deleted for the cbh1, cbh2, egl1, and egl2 genes as described by Bower et al (Carbohydrases from *Trichoderma reesei* and other micro-organisms, Royal Society of Chemistry, Cambridge, 1998, p. 327-334). The plasmid was inserted into spores of *T. reesei* using a biolistic transformation procedure. DNA-coated tungsten particles were prepared as follows. 60 mg of M10 tungsten particles were added to 1 ml ethanol (70% or 100%) in a microcentrifuge tube. This mixture was allowed to soak for 15 minutes, followed by centrifugation for 15 min at 15,000 rpm. The supernatant was then decanted and the pellet washed three times with sterile distilled water. The majority of the distilled water was removed after the final wash. The pellet was then resuspended in 1 ml of a 50% glycerol (v/v, sterile) solution. While continuously vortexing a 25 ul aliquot of this particle suspension was removed and placed in a microcentrifuge tube. To this tube the following components were added (while continuously vortexing) in the following order. 0.5-5 ul of pPGamdS DNA solution (1 ug/ul), 25 ul 2.5M CaCl2, and 10 ul 0.1M spermidine. The mixture was allowed to coat the particles for 5-15 minutes during continuous vortexing, and was used as soon as possible to avoid tungsten degradation of the DNA. The mixture was then centrifuged for approximately three seconds. The supernatant was then removed and the pellet was washed with approx 200 ul of 70% ethanol (v/v) followed by a 3 second centrifugation and removal of the supernatant. The pellet was again washed with 200 ul of 100% ethanol, followed by another 3 second centrifugation. The supernatant was removed and the pellet was then resuspended in 24 ul 100% ethanol and mixed by pipetting. 8 ul aliquots were placed onto macrocarrier discs (Bio-Rad, Hercules, Calif.) by pipetting the aliquots in the exact center of the disks while the disks were in a dessicator. The discs were kept in a dessicator until thoroughly dry and kept there until immediately before use. The macrocarrier discs were inserted into a Model PDS-1000/He Biolistic Particle Delivery System (Bio-Rad, Hercules, Calif.). This apparatus was used according to the manufacturer's directions to propel the DNA-coated tungsten particles at the *T. reesei* spores prepared as below.

A spore suspension of strain the *Trichoderma* strain was made with approximately $5 \times 10^8$ spores/ml. 100-200 ul aliquots of the spore suspension was spread over an area approximately 6 cm in diameter at the center of a plate of agar medium containing acetamide as sole nitrogen source. After the biolistic transformation, the plates were placed in a 28° C. incubator for 4 days. Transformant colonies were able to grow due to incorporation and expression of the amdS gene encoding acetamidase. Transformants were transferred onto fresh agar plates with acetamide as sole nitrogen source and incubated at 28° C. before transfer to liquid defined culture medium.

Liquid defined (LD) culture medium contained the following components. Casamino acids, 9 g/L; $(NH_4)_2SO_4$, 5 g/L; $MgSO_4.7H_2O$, 1 g/L; $KH_2PO_4$, 4.5 g/L; $CaCl_2.2H_2O$, 1 g/L; PIPPS, 33 g/L, 400× *T. reesei* trace elements, 2.5 ml/L; pH adjusted to 5.5 with NaOH. 400× *T. reesei* trace elements solution contained the following: citric Acid (anhydrous), 175 g/L; $FeSO_4.7 H_2O$, 200 g/L, $ZnSO_4.7 H_2O$, 16 g/L, $CuSO_4.5 H_2O$, 3.2 g/L; $MnSO_4.H_2O$, 1.4 g/L; $H_3BO_3$, 0.8 g/L. After sterilization, lactose, glucose or a glucose/sophorose mixture was added to a final concentration of 1.6% w/v.

Twenty four morphologically stable transformant colonies on agar medium were inoculated into LD medium with lactose. After 5 days of growth at 28° C. the secreted proteins were analyzed by polyacrylamide gel electrophoresis (SDS-PAGE) of culture supernatant samples. Those transformants that showed an obvious band on SDS-PAGE corresponding in size to the *T. reesei* glucoamylase protein, which was absent in culture supernatant from the *T. reesei* parent strain, were identified. Transformant PGamdS-8 was chosen as the best producer of glucoamylase.

Transformant PGamdS-8 was cultured in shake flasks under a variety of conditions to determine the effect of carbon source and temperature on glucoamylase production directed by the stp1 promoter. From a colony on agar medium one square cm was excised and used to inoculate 50 ml LD medium with glucose in a baffled 250 ml shake flask. After 2 days of growth at 28° C. and 200 rpm, 5 ml of this pre-culture was used to inoculate shake flasks of 50 ml LD medium with lactose, glucose/sophorose mixture or glucose as carbon source. This production culture was grown for 4 days at 28° C. or 37° C. and 200 rpm. Supernatants were collected by centrifugation of the fermentation broth and glucoamylase production was assessed by SDS-PAGE.

Figures 2A, 2B:
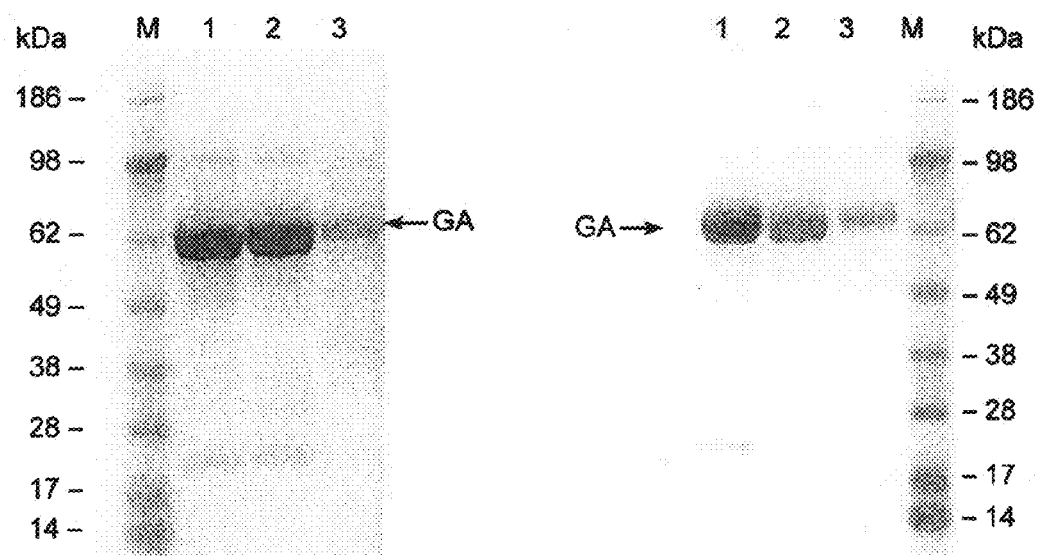
FIG. 2 shows two panels of SDS-PAGE gels of culture supernatants from *T. reesei* strain PGamdS-8 stained with Coomassie Brilliant Blue. M, molecular weight markers; lane 1, growth on lactose as carbon source; lane 2, growth on glucose/sophorose as carbon source; lane 3, growth on glucose as carbon source. A, cultures grown at 28° C.; B, cultures grown at 37° C.

As shown in FIG. 2 a high level of production of glucoamylase was observed when lactose or a mixture of glucose plus sophorose was used as carbon source. Glucoamylase was also observed when glucose was the sole carbon source, albeit at a reduced level, and production was apparent when cultures were grown at either 28° C. or 37° C.

EXAMPLE 3

Expression of *Cerrena unicolor* Laccase in *Trichoderma reesei* Using the stp1 Promoter Expression of the laccase D gene from *Cerrena unicolor* in *Trichoderma reesei* was disclosed in U.S. provisional application GC993P, Ser. No. 60/984,430, "Improved heterologous protein production in a host using signal sequences and co-expressing chaperones" by Genencor, A Danisco Division (herein incorporated by reference in its entirety), which also describes plasmid pKB410. Laccase D expression is further described in WO 08/076,322 published Jun. 28, 2008.

Figure 4:
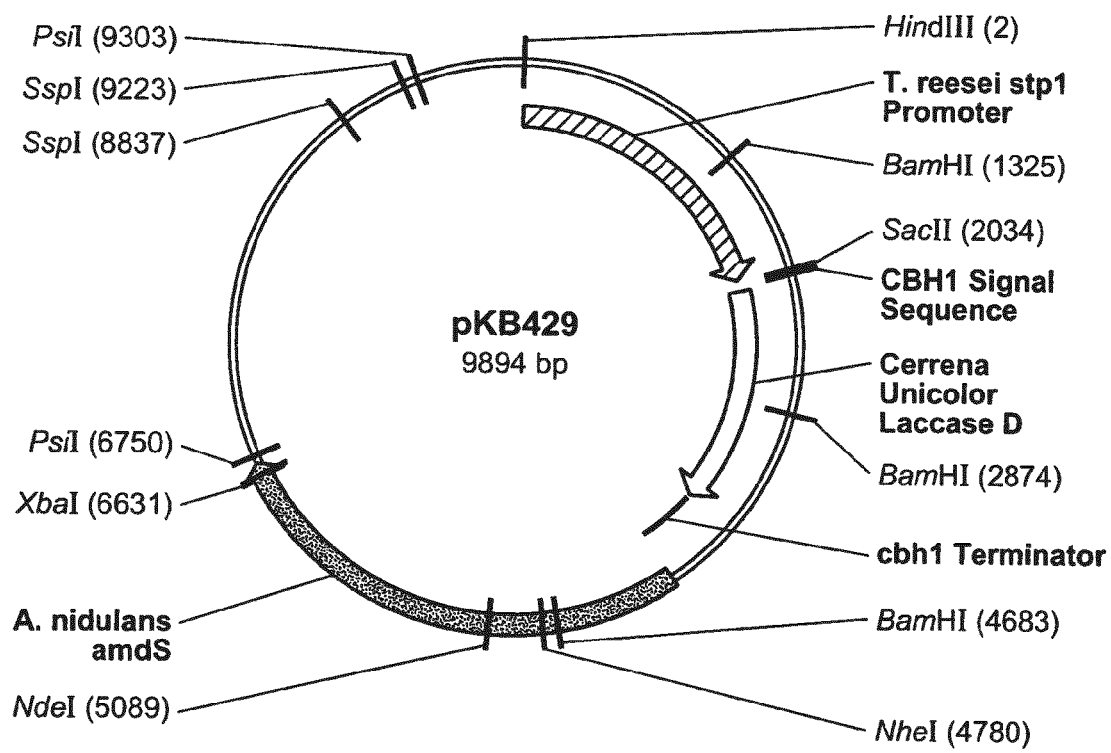
FIG. 4 is a schematic drawing of the plasmid pKB429.

Plasmid pKB410 contains the *T. reesei* cbh1 promoter functionally fused to an open reading frame encoding the *T. reesei* CBHI signal sequence fused to the mature laccase D protein. The plasmid also contains the *Aspergillus nidulans* amdS gene for selection of transformants in *T. reesei*. The cbh1 promoter was removed from pKB410 by digestion with HindIII and SacII and replaced with the 2 kb HindIII—SacII fragment from pPGamdS bearing the *T. reesei* stp1 promoter to create pKB429 (FIG. 4). Plasmids pKB410 and pKB429 were inserted independently into the *Trichoderma reesei* strain by the biolistic transformation procedure as described in Example 2. Ten stable transformants with pKB410 and 14 stable transformants with pKB429 were isolated and screened for secreted laccase D production by measuring activity on ABTS as described in U.S. provisional application GC993P, "Improved heterologous protein production in a host using signal sequences and co-expressing chaperones" by Genencor, A Danisco Division. The four highest producing transformants with each plasmid (designated as clones PCBH1-1, PCBH1-3, PCBH1-6, and PCBH1-9 with pKB410 and Pstp1-2, Pstp1-3, Pstp1-4, and Pstp1-11 with pKB429) were chosen for further study. These transformants were cultured in shake flasks in 50 ml LD medium with lactose as carbon source at 28° C. Supernatant samples were taken each day on days 2 through 8 and the laccase activity on ABTS was measured. As can be seen from Table 1, laccase production using the stp1 promoter was higher than that using the cbh1 promoter.

TABLE 1

Comparison of Laccase D production (ABTS activity in supernatant)

| | cbh1 promoter | | | | stp1 promoter | | | |
|---|---|---|---|---|---|---|---|---|
| | | | | Clone | | | | |
| Day | PCBH1-1 | PCBH1-3 | PCBH1-6 | PCBH1-9 | Pstp1-2 | Pstp1-3 | Pstp1-4 | Pstp1-11 |
| 2 | 0.03 | 0.02 | 0.04 | 0.02 | 0.04 | 0.05 | 0.03 | 0.07 |
| 3 | 0.23 | 0.19 | 0.23 | 0.17 | 0.27 | 0.27 | 0.31 | 0.32 |
| 4 | 0.77 | 0.50 | 0.81 | 0.58 | 1.01 | 1.18 | 0.60 | 1.59 |
| 5 | 1.55 | 2.37 | 1.59 | 1.27 | 2.16 | 2.42 | 3.68 | 2.79 |
| 6 | 2.11 | 1.84 | 2.23 | 1.72 | 3.10 | 3.18 | 5.98 | 3.68 |
| 7 | 2.74 | 2.27 | 2.51 | 2.08 | 3.58 | 3.84 | 7.00 | 4.48 |
| 8 | 3.09 | 2.51 | 2.85 | 2.25 | 3.92 | 4.18 | 8.45 | 5.12 |

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

<160> NUMBER OF SEQ ID NOS: 9

<210> SEQ ID NO 1
<211> LENGTH: 2132
<212> TYPE: DNA
<213> ORGANISM: Trichoderma reesei

<400> SEQUENCE: 1

| | | | | | |
|---|---|---|---|---|---|
| tggcaagtat | ctgctggaaa | aggcccgcgt | ggccgattac | tatgtcgacc | cggtccatcc | 60 |
| ccatgccatt | agcaatgtcg | aggcggacaa | gctgtgggag | ctgagtgtca | aggcagttgg | 120 |
| actgtaggaa | tgaccgtcag | gagacgacgg | aaattacaag | atgatcttga | tgtcgaagat | 180 |
| ggaaattatt | gcagtgagat | gtgaacaaga | ctaggtatac | cttagcaaaa | caaacgagca | 240 |
| ttctcaaaga | atcattggag | tagaggtaca | gaatgccaag | tattccgcac | gcatgttagc | 300 |
| tgcagccaac | tgctagttca | tcaggcaaag | ggcattcgga | gaatctctca | gcatgatgcc | 360 |
| cattttgtcg | acgcacatgg | cttttttactc | cgcatggcgt | ttctattatt | ggtcaatgct | 420 |
| gttctgaagt | cacctccgta | ttccgacatc | agcacatcac | gactatattc | gcctaccctg | 480 |
| gaactcgtcg | cttttccttc | ccaacggccc | gactaaaccg | ttacgagatg | atgaactaac | 540 |
| cccaggtggc | gccggcgggg | cttttccccc | atgtctcctt | gggccaatca | ctgatgcatg | 600 |
| aaattcggca | gcgtcccgga | acgggtaaat | ggacgttgat | gcttccctgt | cgaagcagga | 660 |
| ccttgtcttt | tgtctttgtc | tttgtctttg | tctcttcatg | tggcacattc | catggcttca | 720 |
| gatctaagct | acgtgacctt | ttctcagcta | gtagtacctt | agtactaaat | agtatttttga | 780 |
| ggtattggca | gcaaatctat | tcagcttcag | cttggcaact | gctctttccc | agcaattgtg | 840 |
| cccagtgatt | ggtgaatgat | ccgatcatac | ctgccattag | ccgaaccgaa | tgcaaggctg | 900 |
| tacctgttac | tttgtacctt | accttcttct | caacctcgtg | attcttgccg | tctcttccac | 960 |
| ctgtaccttt | cctcatcatc | tcaagtctac | cgaaccgcca | gctcccccat | acgccatgg | 1020 |
| atggctgttc | tatctcgcca | ccagccgaac | cagcctcaga | agcaatggaa | tcactctctt | 1080 |
| cttttctccc | cttgccttct | tatgctcagc | tttcacggcc | ctccagtcag | ctcgccttct | 1140 |
| tcacacctag | gttcgccatc | tgacatgcaa | ccagggcaaa | ccaccaccac | caaccaccac | 1200 |
| caccaccacc | caaacttcca | aatacttccaa | tcctctgcat | cgtgtcatct | ccatgcctcc | 1260 |
| atacctcctc | ctcctcctcc | ccacgccagc | cagaagcagc | aaggccatgt | aggatttctc | 1320 |
| cgttcgtcgc | gtggcctcgg | cccaatcgtc | agcctgaca | cctccagatt | ccccagaggc | 1380 |
| ggatgatccg | caccacttag | gctaatctct | attcactgga | tccgtctgtc | cagacgaagc | 1440 |
| gccgggctca | ggccaaagct | atccccaaac | catgcccgcc | caacaggcgg | accacaatcc | 1500 |
| tccgcgcctg | catctggctt | gggggggcct | ggtccccgc | attgtggcca | gggccggcca | 1560 |
| gtcgacgcca | cggcacgacg | ccgccgtcca | atagctgctt | caccgcacgc | gtgtgagcgc | 1620 |
| agcaacgcag | cgcgggaaac | ggtgcaaagg | atgggaaaag | ggacaacggc | cgtataagcg | 1680 |
| gcagagcctg | cccgctgagt | cctggccagc | ttcctctgcc | aaataatccg | cccgtgttca | 1740 |
| cctgctccgg | cgaaactcag | ctccaacatg | gcttgaccaa | ctgatgctgc | caggccttca | 1800 |
| ttcgtgctgc | gacgcttcgc | ctgttcggcc | ctattgacaa | gggccatttc | ctcgatagtt | 1860 |
| actcgcccaa | atcgcctggg | gaaggatcac | acgcggcaag | ggaacgagga | cacgagatag | 1920 |
| acataaaagc | ggtagcaccc | cctggccatc | cagactgcaa | cctcacctttt | tttccctctt | 1980 |
| ctctcctcac | cccatcacaa | ctcgccagtt | cccttgactc | tccttcacct | cagaagaaag | 2040 |
| ggggcgtttt | gtgcagcaat | tgctttcctt | caacgctgcc | tccccgactg | aagcgctgtc | 2100 |

```
tctggcccag aggctagaga ttacccgtaa ca                                    2132

<210> SEQ ID NO 2
<211> LENGTH: 1981
<212> TYPE: DNA
<213> ORGANISM: Trichoderma reesei

<400> SEQUENCE: 2
atgggcgaga aagaagacat tcacgctcac gaggagctcg accatgtaag tcaatttgcc       60
caatgatcat ttttacttcc ccttccctct tgttttgcca cctcgcttgg aggagtgagt      120
ctgcttacac catcttctct tgttttgcct gagtagggag agatcaggac caaggtcgtg      180
accggacacg aggcctttga ggaggccatg atgaaggagc cgcccaaggc ctggaccaag      240
gctcaggtcc tcgtctacag cttctccatc attgccttct tctgcagcac catgaacggc      300
tacgacggct cgctcatcaa caacctgctg cagaacccct ggttcaaggc caagtacact      360
gtgggaaacg acggcatctg gccggcatt gtgtcttcca tgtaccagat tggtggtgtc      420
gtcgcccttc cctttgtcgg ccctgccatt gacggctttg ccgccgaat cggcatgctg      480
ttgggtgcca tcctcattgt cgtcggcacc atcatccagg tctgtcaaa ctcgcagggc      540
cagttcatgg gcggccgctt tctgcttgga ttcgcgtcct ccattgcagc ggcagcgggc      600
cccatgtacg tggttgagat taaccaccct gcataccgtg gacgcgttgg cggtaagtat      660
ccattgaccc tcgttctctt ctaatgtctt ttcctccttc attcccaaac ccaatggtgc      720
aggaagggag acagtggagg aaatggacag aaagacatca agcttcaccc gatgctcaac      780
agtcaagtat ggaatcaata gactaacttt cttcttccct gtccctagcc atgtacaaca      840
ctctctggtt ctcgggtgcc atcatctcgg ccggtgccgc tcgaggcggc ctcaacgtcg      900
gaggcgacta ctcgtggcga ctcatcacct ggctccaggc cctcttctcc ggcctcatca      960
tcatcttctg catgttcctg cccgagtccc ccgctggcct acgtgcac cacaagaagg     1020
acgccgccaa ggctgtgctc accaagtatc atggcaacgg aaaccccgac tccgtctggg     1080
tccagctcca gctcttcgag tatgagcagc tcctcaacat ggacggcgcc gataagcgct     1140
ggtgggatta ccgggcgctc ttccgctcgc gcgccgccgt ctaccgtctg ttgtgcaacg     1200
tcaccatcac catttttggc cagtgggctg gcaatgcggt tctttcctac ttcctcggct     1260
ccgtcctcga tacggccggc tacacgggca ccattgcgca ggccaacatc acgctcatca     1320
acaactgcca gcagttcgcc tgggccattc tgggcgcctt cctggtcgac cgcgttggtc     1380
gtcgcccctt gctgctcttc tcctttgctg cctgcaccgt ggtctggctg gcatgacgg     1440
ttgcctcatc cgaatttgcg cagtcgttca tcggaaatga cgccaacggc gatcccatct     1500
acagcaaccc cagcgcttcc aaggctgccc tggccatgat cttcatcttt ggtgccgtct     1560
actctgtggg catcactcct ctgcaggccc tgtatcccgt cgaggtgctc tcctttgaga     1620
tgcgcgccaa gggcatggcc ttttccagct ttgccaccaa cgctgctgga ctcctgaacc     1680
agtttgcatg gccccgtgtcc atggacaaga ttggctggaa gacgtacatt atctttacca     1740
tctgggatct cgtccagacg gttgtcgtct acttttcat tcccgagacc aagggacgca     1800
ctgtaagtgt tgccaactca accatccttt tccatggcat gtctctgacc cattgctttc     1860
tctacagttg gaagagcttg acgaaatctt cgaggccaag aacccggtca agacgtcgac     1920
gacgaagaag gccgtggccg tggacagcca cggcgacatt gtcaatatcg agaaggctta     1980
a                                                                      1981
```

```
<210> SEQ ID NO 3
<211> LENGTH: 1629
<212> TYPE: DNA
<213> ORGANISM: Trichoderma reesei

<400> SEQUENCE: 3
atgggcgaga aagaagacat tcacgctcac gaggagctcg accatggaga gatcaggacc      60
aaggtcgtga ccggacacga ggcctttgag gaggccatga tgaaggagcc gcccaaggcc     120
tggaccaagg ctcaggtcct cgtctacagc ttctccatca ttgccttctt ctgcagcacc     180
atgaacggct acgacggctc gctcatcaac aacctgctgc agaaccctg gttcaaggcc      240 aagtacactg tgggaaacga cggcatctgg gccggcattg tgtcttccat gtaccagatt     300
ggtggtgtcg tcgcccttcc ctttgtcggc cctgccattg acggctttgg ccgccgaatc     360
ggcatgctgt tgggtgccat cctcattgtc gtcggcacca tcatccaggg tctgtcaaac     420
tcgcagggcc agttcatggg cggccgcttt ctgcttggat cggcgtctc cattgcagcg      480 gcagcgggcc ccatgtacgt ggttgagatt aaccaccctg cataccgtgg acgcgttggc     540
gccatgtaca acactctctg gttctcgggt gccatcatct cggccggtgc cgctcgaggc     600
ggcctcaacg tcgaggcgga ctactcgtgg cgactcatca cctggctcca ggccctcttc     660
tccggcctca tcatcatctt ctgcatgttc ctgcccgagt cccccgctg gctctacgtg      720 caccacaaga aggacgccgc caaggctgtg ctcaccaagt atcatggcaa cggaaacccc     780
gactccgtct gggtccagct ccagctcttc gagtatgagc agctcctcaa catggacggc     840
gccgataagc gctggtggga ttaccgggcg ctcttccgct cgcgcgccgc cgtctaccgt     900
ctgttgtgca acgtcaccat caccattttt ggccagtggg ctggcaatgc ggttctttcc     960
tacttcctcg gctccgtcct cgatacggcc ggctacacgg caccattgc gcaggccaac    1020 atcacgctca tcaacaactg ccagcagttc gcctgggcca ttctgggcgc cttcctggtc    1080
gaccgcgttg gtcgtcgccc cttgctgctc ttctcctttg ctgcctgcac cgtggtctgg    1140
ctgggcatga cggttgcctc atccgaattt gcgcagtcgt tcatcggaaa tgacgccaac    1200
ggcgatccca tctacagcaa ccccagcgct tccaaggctg ccctggccat gatcttcatc    1260
tttggtgccg tctactctgt gggcatcact cctctgcagg ccctgtatcc cgtcgaggtg    1320
ctctcctttg agatgcgcgc caagggcatg gccttttcca gctttgccac caacgctgct    1380
ggactcctga ccagtttgc atggcccgtg tccatggaca agattggctg gaagacgtac     1440
attatcttta ccatctggga tctcgtccag acggttgtcg tctactttt cattcccgag     1500 accaagggac gcactttgga gagcttgac gaaatcttcg aggccaagaa cccggtcaag    1560
acgtcgacga cgaagaaggc cgtggccgtg gacagccacg cgacattgt caatatcgag     1620 aaggcttaa                                                            1629

<210> SEQ ID NO 4
<211> LENGTH: 509
<212> TYPE: PRT
<213> ORGANISM: Trichoderma reesei

<400> SEQUENCE: 4

Met Lys Glu Pro Pro Lys Ala Trp Thr Lys Ala Gln Val Leu Val Tyr
1               5                   10                  15

Ser Phe Ser Ile Ile Ala Phe Phe Cys Ser Thr Met Asn Gly Tyr Asp
            20                  25                  30

Gly Ser Leu Ile Asn Asn Leu Leu Gln Asn Pro Trp Phe Lys Ala Lys
        35                  40                  45
```

```
Tyr Thr Val Gly Asn Asp Gly Ile Trp Ala Gly Ile Val Ser Ser Met
     50                  55                  60
Tyr Gln Ile Gly Gly Val Ala Leu Pro Phe Val Gly Pro Ala Ile
 65              70                  75                  80
Asp Gly Phe Gly Arg Arg Ile Gly Met Leu Leu Gly Ala Ile Leu Ile
                 85                  90                  95
Val Val Gly Thr Ile Ile Gln Gly Leu Ser Asn Ser Gln Gly Gln Phe
            100                 105                 110
Met Gly Gly Arg Phe Leu Leu Gly Phe Gly Val Ser Ile Ala Ala Ala
            115                 120                 125
Ala Gly Pro Met Tyr Val Glu Ile Asn His Pro Ala Tyr Arg Gly
        130                 135                 140
Arg Val Gly Ala Met Tyr Asn Thr Leu Trp Phe Ser Gly Ala Ile Ile
145                 150                 155                 160
Ser Ala Gly Ala Arg Gly Gly Leu Asn Val Gly Gly Asp Tyr Ser
                165                 170                 175
Trp Arg Leu Ile Thr Trp Leu Gln Ala Leu Phe Ser Gly Leu Ile Ile
            180                 185                 190
Ile Phe Cys Met Phe Leu Pro Glu Ser Pro Arg Trp Leu Tyr Val His
        195                 200                 205
His Lys Lys Asp Ala Ala Lys Ala Val Leu Thr Lys Tyr His Gly Asn
    210                 215                 220
Gly Asn Pro Asp Ser Val Trp Val Gln Leu Gln Leu Phe Glu Tyr Glu
225                 230                 235                 240
Gln Leu Leu Asn Met Asp Gly Ala Asp Lys Arg Trp Trp Asp Tyr Arg
                245                 250                 255
Ala Leu Phe Arg Ser Arg Ala Ala Val Tyr Arg Leu Leu Cys Asn Val
                260                 265                 270
Thr Ile Thr Ile Phe Gly Gln Trp Ala Gly Asn Ala Val Leu Ser Tyr
            275                 280                 285
Phe Leu Gly Ser Val Leu Asp Thr Ala Gly Tyr Thr Gly Thr Ile Ala
        290                 295                 300
Gln Ala Asn Ile Thr Leu Ile Asn Asn Cys Gln Gln Phe Ala Trp Ala
305                 310                 315                 320
Ile Leu Gly Ala Phe Leu Val Asp Arg Val Gly Arg Arg Pro Leu Leu
                325                 330                 335
Leu Phe Ser Phe Ala Ala Cys Thr Val Val Trp Leu Gly Met Thr Val
                340                 345                 350
Ala Ser Ser Glu Phe Ala Gln Ser Phe Ile Gly Asn Asp Ala Asn Gly
            355                 360                 365
Asp Pro Ile Tyr Ser Asn Pro Ser Ala Ser Lys Ala Ala Leu Ala Met
        370                 375                 380
Ile Phe Ile Phe Gly Ala Val Tyr Ser Val Gly Ile Thr Pro Leu Gln
385                 390                 395                 400
Ala Leu Tyr Pro Val Glu Val Leu Ser Phe Glu Met Arg Ala Lys Gly
                405                 410                 415
Met Ala Phe Ser Ser Phe Ala Thr Asn Ala Ala Gly Leu Leu Asn Gln
            420                 425                 430
Phe Ala Trp Pro Val Ser Met Asp Lys Ile Gly Trp Lys Thr Tyr Ile
        435                 440                 445
Ile Phe Thr Ile Trp Asp Leu Val Gln Thr Val Val Tyr Phe Phe
450                 455                 460
Ile Pro Glu Thr Lys Gly Arg Thr Leu Glu Glu Leu Asp Glu Ile Phe
465                 470                 475                 480
```

```
Glu Ala Lys Asn Pro Val Lys Thr Ser Thr Thr Lys Lys Ala Val Ala
            485                 490                 495

Val Asp Ser His Gly Asp Ile Val Asn Ile Glu Lys Ala
            500                 505

<210> SEQ ID NO 5
<211> LENGTH: 35
<212> TYPE: DNA
<213> ORGANISM: Artificial
<220> FEATURE:
<223> OTHER INFORMATION: synthetic primer

<400> SEQUENCE: 5
ggccaagctt gagctgagtg tcaaggcagt tgcac                              35

<210> SEQ ID NO 6
<211> LENGTH: 36
<212> TYPE: DNA
<213> ORGANISM: Artificial
<220> FEATURE:
<223> OTHER INFORMATION: synthetic primer

<400> SEQUENCE: 6
gggaccgcgg taatctctag cctctgggcc agagac                             36

<210> SEQ ID NO 7
<211> LENGTH: 44
<212> TYPE: DNA
<213> ORGANISM: Artificial
<220> FEATURE:
<223> OTHER INFORMATION: synthetic primer

<400> SEQUENCE: 7
gtcgacagga cgtgcattgt taccgcggta atctctagcc tctg                    44

<210> SEQ ID NO 8
<211> LENGTH: 44
<212> TYPE: DNA
<213> ORGANISM: Artificial
<220> FEATURE:
<223> OTHER INFORMATION: synthetic primer

<400> SEQUENCE: 8
cagaggctag agattaccgc ggtaacaatg cacgtcctgt cgac                    44

<210> SEQ ID NO 9
<211> LENGTH: 36
<212> TYPE: DNA
<213> ORGANISM: Artificial
<220> FEATURE:
<223> OTHER INFORMATION: synthetic primer

<400> SEQUENCE: 9
cgcggcgcgc cttacgactg ccaggtgtcc tccttg                             36
```

It is claimed:

1. An isolated nucleic acid comprising a truncated form of the nucleotide sequence of SEQ ID NO: 1 that has promoter activity in a filamentous fungal host cell, wherein the truncated SEQ ID NO: 1 nucleotide sequence comprises at least 800 contiguous nucleotides and retains promoter activity.

2. The isolated nucleic acid of claim 1, comprising at least 1000 contiguous nucleotides of SEQ ID NO:1.

3. The isolated nucleic acid of claim 1, comprising at least 1200 contiguous nucleotides of SEQ ID NO:1.

4. The isolated nucleic acid of claim 1, comprising at least 1500 contiguous nucleotides of SEQ ID NO:1.

5. The isolated nucleic acid of claim 1, comprising at least one putative transcription factor binding site of SEQ ID NO:1.

6. The isolated nucleic acid of claim 5, comprising a first and a second transcription factor binding sites of SEQ ID NO:1.

7. The isolated nucleic acid of claim 5, comprising the sequence from the start of the positive regulatory transcription factor binding site through the transcription start site.

8. The isolated nucleic acid of claim 1, wherein said nucleic acid hybridizes under high stringency conditions with a polynucleotide having the nucleotide sequence of SEQ ID NO: 1.

9. A recombinant nucleic acid comprising the isolated nucleic acid of claim 1, and a polynucleotide encoding a protein, wherein said isolated nucleic acid and said polynucleotide are operably linked such that said isolated nucleic acid causes transcription of said polynucleotide in a filamentous fungal host cell.

10. The recombinant nucleic acid of claim 9, wherein said protein is an enzyme.

11. The recombinant nucleic acid of claim 10, wherein said enzyme is a glucoamylase, an amylase, a cellulase, a protease, a xylanase, a lipase, a phytase, a hemicellulase, a pectinase, a catalase, an oxidase, a glucanase, a glycosidase, or a laccase.

12. The recombinant nucleic acid of claim 9, wherein said protein is a therapeutic protein.

13. A nucleic acid vector comprising the recombinant nucleic acid of claim 10.

14. A host cell comprising the recombinant nucleic acid of claim 10.

15. The host cell of claim 14, wherein said host cell is an *Aspergillus* sp., a *Trichoderma* sp., a *Humicola* sp., or a *Fusarium* sp. host cell.

16. The host cell of claim 15, wherein said host cell is a *Trichoderma* sp. host cell.

17. The host cell of claim 16, wherein the *Trichoderma* sp. host cell is a *Trichoderma reesei* host cell.

18. A method of producing a protein comprising, transforming a filamentous fungal host cell with the recombinant nucleic acid of claim 10, culturing the host cell under suitable culture conditions to allow transcription, translation and thereby production of the protein.

19. The method of claim 18, further comprising recovering said protein from said culture.

20. The isolated nucleic acid of claim 1, wherein the filamentous fungal host cell is a *Trichoderma reesei* host cell.

* * * * *